United States Patent [19]

Kehne et al.

[11] Patent Number: 5,576,440
[45] Date of Patent: Nov. 19, 1996

[54] 2-PYRIDYLSULFONAMIDES

[75] Inventors: Heinz Kehne, Hofheim am Taunus; Lothar Willms, Hillscheid; Oswald Ort, Kelkheim/Taunus; Klaus Bauer, Hanau; Hermann Bieringer, Eppstein/Taunus, all of Germany

[73] Assignee: Hoechst Aktiengesellschaft, Germany

[21] Appl. No.: 368,742

[22] Filed: Jan. 4, 1995

Related U.S. Application Data

[60] Continuation of Ser. No. 108,480, Aug. 18, 1993, abandoned, which is a division of Ser. No. 859,513, filed as PCT/EP90/02308, Dec. 24, 1990.

[30] Foreign Application Priority Data

Jan. 10, 1990 [DE] Germany ............... 40 00 503.8
Sep. 27, 1990 [DE] Germany ............... 40 30 557.5

[51] Int. Cl.$^6$ .................. C07D 213/71; C07D 409/12; C07D 417/04
[52] U.S. Cl. .................. 546/294; 546/291; 546/293; 546/272.4; 546/261; 546/193; 546/278.4; 546/271.1; 544/60; 544/3; 544/209; 544/212; 544/320; 544/331; 544/278; 544/219; 544/131; 504/213; 504/215; 504/216
[58] Field of Search .................. 546/294, 291, 546/280; 544/60

[56] References Cited

U.S. PATENT DOCUMENTS

| | | | |
|---|---|---|---|
| 4,421,550 | 12/1983 | Selby et al. | 504/211 |
| 4,487,626 | 12/1984 | Zimmerman | 504/215 |
| 4,946,494 | 8/1990 | Taylor | 504/213 |
| 5,139,565 | 8/1992 | Kimura et al. | 504/215 |

FOREIGN PATENT DOCUMENTS

| | | | |
|---|---|---|---|
| 0013480B1 | 7/1980 | European Pat. Off. | 504/215 |
| 0084224B1 | 7/1983 | European Pat. Off. | 504/134 |
| 0103543A2 | 3/1984 | European Pat. Off. | 504/215 |
| 0125864B1 | 11/1984 | European Pat. Off. | 504/214 |
| 0178101B1 | 4/1986 | European Pat. Off. | 504/215 |
| 0272855B1 | 6/1988 | European Pat. Off. | 504/215 |
| 0314505 | 5/1989 | European Pat. Off. | 504/215 |
| 0451468A1 | 10/1991 | European Pat. Off. | 546/291 |
| 4000503A1 | 7/1991 | Germany | 504/244 |
| WO88/04297 | 6/1988 | WIPO | 504/244 |
| WO90/06308 | 6/1990 | WIPO | 504/215 |
| WO91/10660 | 7/1991 | WIPO | 504/215 |

OTHER PUBLICATIONS

Kehne et al., Chemical Abstract, vol. 115: 183348e.

*Primary Examiner*—Alan L. Rotman
*Attorney, Agent, or Firm*—Curtis, Morris & Safford, P.C.

[57] ABSTRACT

Compounds of formula (I), where $R^1$, $R^2$, n, W, $R^3$ and A are as defined in claim 1, are suitable for use as herbicides and plant growth regulators. They can be produced by a process similar to known processes. To produce them, new compounds of formula (II) are reacted with a carbamate of formula R*—O—CO—NR$^3$A, where $R^3$ stands for phenyl or alkyl. The compounds of formula (II) can be obtained from the corresponding sulphochlorides.

65 Claims, No Drawings

2-PYRIDYLSULFONAMIDES

This application is a continuation of application Ser. No. 08/108,480, filed Aug. 18, 1993, abandoned which in turn is a divisional of application Ser. No. 07/859,513, filed as PCT/JP90/02308 Dec. 24, 1990.

It is known that some 2-pyridylsulfonylureas have herbicidal and plant growth-regulating properties; cf. EP-A-13,480, EP-A-272,855, EP-A-84,224, U.S. Pat. No. 4,421,550, EP-A-103,543 (U.S. Pat. No. 4,579,583), U.S. Pat. No. 4,487,626, EP-A-125,864, WO 88/04297.

It has now been found that 2-pyridylsulfonylureas having specific radicals in the 3-position of the pyridyl radical are particularly highly suitable as herbicides and growth regulators.

The present invention relates to compounds of the formula (I) or their salts

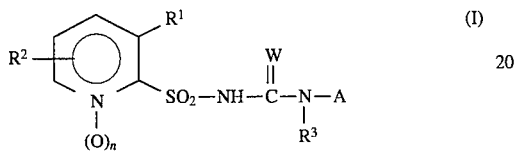

in which $R^1$ is $-OSO_2NR^4R^5$, $-NR^6R^7$ or iodine, $R^2$ is H, $(C_1-C_4)$alkyl, preferably $(C_1-C_3)$alkyl, $(C_1-C_3)$haloalkyl, halogen, $NO_2$, CN, $(C_1-C_3)$alkoxy, $(C_1-C_3)$haloalkoxy, $(C_1-C_3)$alkylthio, $(C_1-C_3)$alkoxy$(C_1-C_3)$alkyl, $(C_1-C_3)$alkoxycarbonyl, $(C_1-C_3)$alkylamino, di-$[(C_1-C_3)$alkyl]amino, $(C_1-C_3)$alkylsulfinyl, $(C_1-C_3)$alkylsulfonyl, $SO_2NR^aR^b$ or $C(O)NR^aR^b$, $R^a$ and $R^b$ independently of one another are H, $(C_1-C_3)$alkyl, $(C_3-C_4)$alkenyl, propargyl, or together are $-(CH_2)_4-$, $-(CH_2)_5-$ or $-CH_2CH_2OCH_2CH_2-$, $R^3$ is H or $CH_3$, $R^4$ is H, $(C_1-C_3)$alkyl, $(C_3-C_4)$alkenyl, $(C_1-C_3)$alkoxy or $(C_3-C_4)$alkynyl, preferably propargyl, and $R^5$ is H, $(C_1-C_3)$alkyl, $(C_3-C_4)$alkenyl or $(C_3-C_4)$alkynyl, preferably propargyl, or $R^4$ and $R^5$ together are $-(CH_2)_4-$, $-(CH_2)_5-$ or $-CH_2CH_2OCH_2CH_2-$, $R^6$ is H, $(C_1-C_8)$alkyl, which is unsubstituted or substituted by one or more radicals from the group comprising halogen, $(C_1-C_4)$alkoxy, $(C_1-C_4)$alkylthio, $(C_1-C_4)$alkylsulfinyl, $(C_1-C_4)$alkylsulfonyl, $(C_1-C_4$-alkoxy)carbonyl and CN, $(C_3-C_6)$alkenyl which is unsubstituted or substituted by one or more halogen atoms, $(C_3-C_6)$alkynyl which is unsubstituted or substituted by one or more halogen atoms, $(C_1-C_4)$alkylsulfonyl which is unsubstituted or substituted by one or more halogen atoms, phenylsulfonyl where the phenyl radical is unsubstituted or substituted by one or more radicals from the group comprising halogen, $(C_1-C_4)$alkyl and $(C_1-C_4)$alkoxy, $(C_1-C_4)$alkoxy or $(C_1-C_4$-alkyl)carbonyl which is unsubstituted or substituted by one or more halogen atoms, $R^7$ is $(C_1-C_4)$alkylsulfonyl which is unsubstituted or substituted by one or more halogen atoms, phenylsulfonyl where the phenyl radical is unsubstituted or substituted by one or more radicals from the group comprising halogen, $(C_1-C_4)$alkyl and $(C_1-C_4)$alkoxy, or di-$[(C_1-C_4)$alkyl]aminosulfonyl or $R^6$ and $R^7$ together are a chain of the formula $-(CH_2)_m-SO_2-$, where the chain can additionally be substituted by 1 to 4 $(C_1-C_3)$alkyl radicals and m is 3 or 4, n is zero or 1, W is O or S, A is a radical of the formula

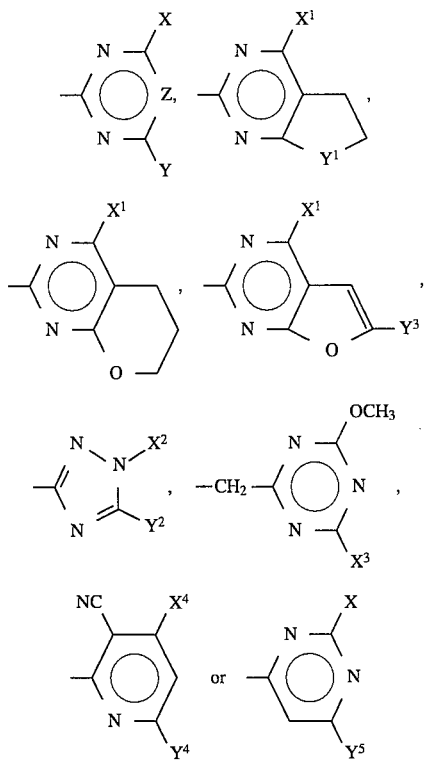

X is H, halogen, $(C_1-C_3)$alkyl, $(C_1-C_3)$alkoxy, where the two last-mentioned radicals are unsubstituted or monosubstituted or polysubstituted by halogen or monosubstituted by $(C_1-C_3)$alkoxy, Y is H, $(C_1-C_3)$alkyl, $(C_1-C_3)$alkoxy or $(C_1-C_3)$alkylthio, where the abovementioned alkyl-containing radicals are unsubstituted or monosubstituted or polysubstituted by halogen or monosubstituted or disubstituted by $(C_1-C_3)$alkoxy or $(C_1-C_3)$alkylthio, and also a radical of the formula $NR^8R^9$, $(C_3-C_6)$cycloalkyl, $(C_2-C_4)$alkenyl, $(C_2-C_4)$alkynyl, $(C_3-C_4)$alkenyloxy or $(C_3-C_4)$alkynyloxy, Z is CH or N, $R^8$ and $R^9$ independently of one another are H, $(C_1-C_3)$alkyl or $(C_3-C_4)$alkenyl, $X^1$ is $CH_3$, $OCH_3$, $OC_2H_5$ or $OCF_2H$, $Y^1$ is $-O-$ or $-CH_2-$, $X^2$ is $CH_3$, $C_2H_5$ or $CH_2CF_3$, $Y^2$ is $OCH_3$, $OC_2H_5$, $SCH_5$, $SC_2H_5$, $CH_3$ or $C_2H_5$, $X^3$ is $CH_3$ or $OCH_3$, $Y^3$ is H or $CH_3$, $X^4$ is $CH_3$, $OCH_3$, $OC_2H_5$, $CH_2OCH_3$ or Cl, $Y^4$ is $CH_3$, $OCH_3$, $OC_2H_5$ or Cl, $Y^5$ is $CH_3$, $C_2H_5$, $OCH_3$ or Cl.

In the formula (I), alkyl, alkoxy, haloalkyl, alkylamino and alkylthio radicals and the corresponding unsaturated and/or substituted radicals can in each case be straight-chain or branched. Alkyl radicals, also in combined meanings such as alkoxy, haloalkyl etc., are methyl, ethyl, n- or i-propyl, alkenyl and alkynyl radicals have the meaning of the possible unsaturated radicals corresponding to the alkyl radicals, such as 2-propenyl, 2- or 3-butenyl, 2-propynyl, 2- or 3-butynyl. Halogen is fluorine, chlorine, bromine or iodine.

The compounds of the formula (I) can form salts in which the hydrogen of the -SO$_2$-NH group is replaced by a cation which is suitable for agricultural purposes. These salts are, for example, metal salts, in particular alkali metal or alkaline earth metal salts, or alternatively ammonium salts or salts with organic amines. Salt formation can also take place by addition of a strong acid to the pyridine moiety of the compound of the formula (I). Suitable acids for this are HCl, HBr, H$_2$SO$_4$ or HNO$_3$.

Preferred compounds of the formula (I) or their salts are those in which n=m zero, W=O and A is a radical of the formula

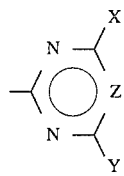

in which X, Y and Z are defined as described above.

Preferred compounds of the formula I or their salts are also those in which

R$^2$, R$^a$, R$^b$, n, W and A are as defined above and

R$^4$ and R$^5$ independently of one another are (C$_1$–C$_3$)alkyl, allyl or propargyl or R$^4$ and R$^5$ together are —(CH$_2$)$_4$—, —(CH$_2$)$_5$— or —CH$_2$CH$_2$OCH$_2$CH$_2$—, R$^5$ is H, (C$_1$–C$_4$)alkyl which is unsubstituted or substituted by one or more halogen atoms or by a radical from the group comprising (C$_1$–C$_3$)alkoxy, (C$_1$–C$_3$)alkylthio, (C$_1$–C$_3$)alkylsulfonyl, (C$_1$–C$_4$)alkoxycarbonyl and CN, (C$_3$–C$_4$)alkenyl, (C$_3$–C$_4$)alkynyl, (C$_1$–C$_4$)alkylsulfonyl, phenylsulfonyl, phenylsulfonyl which is substituted by one to three radicals from the group comprising halogen, (C$_1$–C$_3$)alkyl and (C$_1$–C$_3$)alkoxy, (C$_1$–C$_3$)alkoxy or (C$_1$–C$_4$)alkylcarbonyl, R$^7$ is (C$_1$–C$_4$)alkylsulfonyl, phenylsulfonyl or phenylsulfonyl which is substituted by 1 to 3 radicals from the group comprising halogen, (C$_1$–C$_3$)alkyl and (C$_1$–C$_3$)alkoxy, or di-(C$_1$–C$_4$-alkyl)-aminosulfonyl or and R$^6$ and R$^7$ together are a chain of the formula —(CH$_2$)$_m$SO$_2$— where m is 3 or 4.

Particularly preferred compounds of the formula (I) or their salts are those in which R$^2$ is H, (C$_1$–C$_3$)alkyl, (C$_1$–C$_3$)alkoxy, halogen or (C$_1$–C$_3$)alkylthio, R$^4$ and R$^5$ independently of one another are (C$_1$–C$_3$)alkyl, R$^6$ is hydrogen, (C$_1$–C$_4$)alkyl or (C$_1$–C$_3$)alkylsulfonyl, R$^7$ is (C$_1$–C$_3$)alkylsulfonyl and A is a radical of the formula

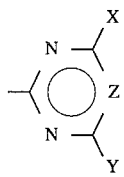

in which Z is CH or N, X is halogen, (C$_1$–C$_2$)alkyl, (C$_1$–C$_2$)alkoxy, OCF$_2$H, CF$_3$ or OCH$_2$CF$_3$ and Y is (C$_1$–C$_2$)alkyl, (C$_1$–C$_2$)alkoxy or OCF$_2$H, and in particular the compounds defined above in which n=zero and W is an oxygen atom.

The present invention further relates to processes for the preparation of the compounds of the formula (I) or their salts, which comprise (a) reacting a compound of the formula (II)

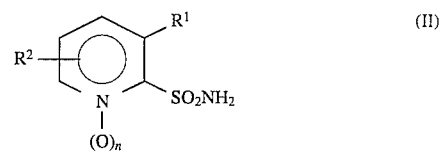

with a heterocyclic carbamate of the formula (III)

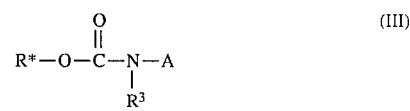

in which R* is phenyl or (C$_1$–C$_4$)alkyl, or (b) reacting a pyridylsulfonylcarbamate of the formula (IV)

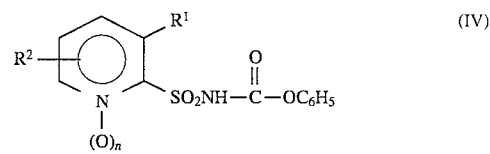

with an aminoheterocycle of the formula (V)

or (c) reacting a sulfonyl isocyanate of the formula (VI)

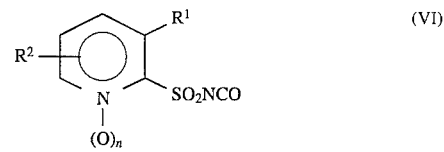

with an aminoheterocycle of the formula R$^3$—NH—A (V) or (d) first reacting an aminoheterocycle of the formula R$^3$—NH—A (V) in a one-pot reaction with phosgene in the presence of a base, such as, for example, triethylamine, and reacting the intermediate formed with a pyridinesulfonamide of the formula (II) (for example analogously to EP-A-232,067).

The reaction of the compounds of the formulae (II) and (III) is preferably carried out under base catalysis in an inert organic solvent, such as, for example, dichloromethane, acetonitrile, dioxane or THF at temperatures between 0° C. and the boiling point of the solvent. 1,8-Diazabicyclo[5.4.0] undec-7-ene (DBU) or trimethylaluminum or triethylaluminum is preferably used as the base.

The sulfonamides (II) are novel compounds. The invention also relates to them and their preparation. They are obtained starting from suitably substituted 2-halopyridines, which are reacted with S-nucleophiles such as, for example, benzylmercaptan or thiourea. The compounds formed in this way are converted with sodium hypochlorite or chlorine into the sulfochlorides (analogously to EP-A-272,855), which are then either reacted directly with ammonia or with tert.-butylamine via the tert.-butylamides with subsequent protective group removal to give-the sulfonamides of the formula (II).

The carbamates of the formula (III) can be prepared by methods which are described in South African patent applications 82/5671 and 82/5045, or EP-A-70804 (U.S. Pat. No. 4,480,101) or RD 275056.

The reaction of the compounds (IV) with the aminoheterocycles (V) is preferably carried out in inert aprotic solvents such as, for example, dioxane, acetonitrile or tetrahydrofuran at temperatures between 0° C. and the boiling point of the solvent. The starting materials (v) required are known from the literature or can be prepared by processes which are known from the literature. The pyridylsulfonylcarbamate of the formula (IV) are obtained analogously to EP-A-44,808 or EP-A-237,292.

The pyridylsulfonylisocyanates of the formula (VI) can be prepared analogously to EP-A-184,385 and reacted with the aminoheterocycles (V).

The salts of the compounds of the formula (I) are preferably prepared in inert solvents such as, for example, water, methanol or acetone at temperatures of 0° –100° C. Suitable bases for the preparation of the salts according to the invention are, for example, alkali metal carbonates, such as potassium carbonate, alkali metal and alkaline earth metal hydroxides, ammonia or ethanolamine. HCl, HBr, $H_2SO_4$ or $HNO_3$ are particularly suitable as acids for salt formation.

By "inert solvents" in the process variants above, solvents are in each case meant which are inert under the particular reaction conditions, but which do not have to be inert under all reaction conditions.

The compounds of the formula (I) according to the invention have an excellent herbicidal activity against a broad spectrum of economically important monocotyledon and dicotyledon weeds. Even perennial weeds, which are difficult to control and shoot from rhizomes, root stocks or other perennial organs, are well controlled by the active compounds. It is irrelevant here whether the substances are applied pro-sowing, pro-emergence or post-emergence. In particular, some representatives of the monocotyledon and dicotyledon weed flora which can be controlled by the compounds according to the invention may be mentioned by way of example without a restriction to certain species being intended by their mention.

On the monocotyledon weed species side, for example, Avena, Lolium, Alopecurus, Phalaris, Echinochloa, Digitaria, Setaria and Cyperus species from the annual group and on the perennial species side Agropyron, Cynodon, Imperata and Sorghum and also perennial Cyperus species are well controlled.

In the case of dicotyledon weed species, the spectrum of action extends to species such as, for example, Galium, Viola, Veronica, Lamium, Stellaria, Amaranthus, Sinapis, Ipomoea, Matricaria, Abutilon and Sida on the annual side and Convolvulus, Cirsium, Rumex and Artemisia in the case of the perennial weeds.

Under the specific cultivation conditions, weeds occurring in rice, such as, for example, Sagittaria, Alisma, Eleocharis, Scirpus and Cyperus are also outstandingly controlled by the active compounds according to the invention.

If the compounds according to the invention are applied to the surface of the soil before germination, the emergence of the weed seedlings is either completely prevented or the weeds grow to the seed leaf stage, but then cease their growth and finally die completely after the passage of three to four weeks.

On application of the active compounds to the green parts of plants post-emergence, a drastic stop to growth also occurs very rapidly after the treatment and the weed plants remain at the growth stage present at the time of application or die completely after a certain time, so that in this manner weed competition which is damaging for the crop plants is eliminated very early and in a lasting manner.

Although the compounds according to the invention have an excellent herbicidal activity against monocotyledon and dicotyledon weeds, crop plants of economically important crops such as, for example, wheat, barley, rye, rice, corn, sugarbeet, cotton and soya are only damaged insubstantially or not at all. For these reasons, the present compounds are very highly suitable for selectively controlling undesired plant growth in agricultural productive plantings.

Moreover, the substances according to the invention show excellent growth regulatory properties in crop plants. They intervene in a regulating manner in the plant's own metabolism and can thus be employed for influencing plant contents in a controlled manner and for simplifying harvesting such as, for example, by causing desiccation and stunting of growth. In addition, they are also suitable for the general control and inhibition of undesired vegetative growth without killing the plants. In many monocotyledon and dicotyledon crops, inhibition of the vegetative growth plays a great role, as lodging can be reduced by this or completely prevented.

The compounds according to the invention can be used in the customary preparations in the form of wettable powders, emulsifiable concentrates, sprayable solutions, dusting agents or granules. The invention therefore also relates to herbicidal and plant growth-regulating agents which contain compounds of the formula (I) or their salts.

The compounds of the formula (I) can be formulated in various ways, depending on which biological and/or physicochemical parameters are given. Examples of suitable formulation possibilities are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting agents (DP), seed dressings, granules for broadcasting and application to the soil, granules (GR) in the form of microgranules, sprayable granules, swellable granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie", volume 7, C. Hauser Verlag Munich, 4th Edition 1986; Wade van Valkenburg, "Pesticide Formulations", Marcel Dekker New York, 1973; K. Martens, "Spray Drying Handbook", 3rd Ed. 1979, G. Goodwin Ltd. London.

The necessary formulation auxiliaries such as inert materials, surfactants, solvents and other additives are also known and are described, for example, in: Watkins, "Handbook of Insecticide Dust Diluents and Carriers", 2nd Ed., Darland Books, Caldwell N.J.; H.v. Olphen, "Introduction to Clay Colloid Chemistry"; 2nd Ed., J. Wiley and Sons, New York; Co Marsden, "Solvents Guide", 2nd Ed., Interscience, New York 1963; McCutcheon's "Detergents and Emulsifiers Annual", MC Publ. Corp., Ridgewood, N.J.; Sisley and Wood, "Encyclopedia of Surface Active Agents", Chem. Publ. Co. Inc., New York 1964; Schönfeldt, "Grenzfl ächenaktive Äthylenoxidaddukte" (Surface-active ethylene oxide adducts), Wiss. Verlagsgesell., Stuttgart 1976; Winnacker-Küchler, "Chemische Technologie" (Chemical Technology), Vol. 7, C. Hauser Verlag Munich, 4th Edition, 1986.

Combinations with other pesticidally active substances, fertilizers and/or growth regulators can also be prepared based on these formulations, for example in the form of a finished formulation or as a tank mix.

Wettable powders are preparations which can be dispersed uniformly in water which apart from the active compound and in addition to a diluent or inert substance also contain wetting agents, for example polyoxyethylated alkylphenols, polyoxyethylated fatty alcohols and fatty amines, fatty alcohol polyglycol ether sulfates, alkane sulfonates or alkylbenzenesulfonate and dispersants, for example sodium ligninsulfonate, sodium 2,2'-dinaphthylmethane-6,6'-disulfonate, sodium dibutylnaphthalenesulfonate or alternatively sodium oleylmethyltaurate.

Emulsifiable concentrates are prepared by dissolving the active compound in an organic solvent, for example butanol, cyclohexanone, dimethylformamide, xylene or alternatively high-boiling aromatics or hydrocarbons with the addition of one or more emulsifiers. Examples of emulsifiers which can be used are: calcium alkylarylsulfonates such as Ca dodecylbenzenesulfonate or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan fatty acid esters, polyoxyethylene sorbitan fatty acid esters, polyoxyethytene sorbitol esters.

Dusting agents are obtained by grinding the active compound with finely divided solid substances, for example talc, natural clays such as kaolin, bentonite and pyrophyllite, or diatomaceous earth.

Granules can be prepared either by spraying the active compound onto adsorptive, granulated inert material or by applying active compound concentrates by means of adhesives, for example polyvinyl alcohol, sodium polyacrylate or alternatively mineral oils, to the surface of carriers such as sand, kaolinites or granulated inert material. Suitable active compounds can also be granulated in the manner customary in the preparation of fertilizer granules, if desired mixed with fertilizer granules.

The agrochemical preparations as a rule contain 0.1 to 99 percent by weight, in particular 0.1 to 95% by weight, of active compound of the formula (I).

In wettable powders the active compound concentration is, for example, about 10 to 90% by weight, the remainder to 100% by weight is composed of customary formulation components. In emulsifiable concentrates, the active compound concentration can be about 1 to 85% by weight, usually 5 to 80% by weight. Pulverulent formulations contain about 1 to 25% by weight, usually 5 to 20% by weight of active compound, sprayable solutions about 0.2 to 20% by weight, usually 2 to 20% by weight of active compound. In the case of granules, the active compound content in some cases depends on whether the active compound is liquid or solid. As a rule, the content in the water-dispersible granules is between 10 and 90% by weight.

In addition, said active compound formulations optionally contain the adhesives, wetting agents, dispersants, emulsifiers, penetrants, solvents, fillers or carriers customary in each case.

For application, the formulations in commercially available form are optionally diluted in a customary manner, for example by means of water in the case of wettable powders, emulsifiable concentrates, dispersions and water-dispersible granules. Pulverulent preparations, granules for application to the soil or broadcasting and sprayable solutions are customarily not diluted further with other inert substances before application.

The required application rate of the compounds of the formula (I) varies, inter alia, with the external conditions such as temperature, humidity and the nature of the herbicide used. It can vary within wide limits, for example between 0.001 and 10.0 kg/ha or more of active substance, but it is preferably between 0.005 and 5 kg/ha.

Mixtures or mixed formulations with other active compounds, such as, for example, insecticides, acaricides, herbicides, safeners, fertilizers, growth regulators or fungicides are also optionally possible.

A. CHEMICAL EXAMPLES

Example 1

2-Benzylthio-3-iodopyridine

A solution of 34.0 g (0.15 mol) of 2-fluoro-3-iodopyridine and 18.6 g (0.15 mol) of benzylmercaptan in 250 ml of acetonitrile is heated under reflux with 22.8 g (0.165 mol) of potassium carbonate for 8 h. The mixture is cooled, the solvent is removed on a rotary evaporator, the residue is taken up in dichloromethane and the organic phase is washed with water. After drying with sodium sulfate, evaporating and distilling the oily residue in vacuo, 37.3 g (76% of theory) of 2-benzylthio-3-iodopyridine of boiling point 150°–153° C. at 0.1 mbar are obtained.

Example 2

3-Iodo-2-pyridinesulfonamide 510 ml (0.34 mol) of a 5% strength sodium hypochlorite solution are added dropwise at 0° C. to a mixture of 25.0 g (76.5 mmol) of 2-benzylthio-3-iodopyridine, 125 ml of dichloromethane, 60 ml of water and 38 ml of concentrated hydrochloric acid. The mixture is stirred at 0° C. for 30min, extracted 3× using 100 ml of dichloromethane each time and the organic phase is dried using sodium sulfate. The solution thus obtained is cooled to −20° C. 6.8 g (0.4 mol) of ammonia is passed in at this temperature in the course of 20 min, and the mixture is stirred at −20° C. for 2 h and allowed to come to room temperature. The reaction mixture is washed with water and the organic phase is dried and evaporated. Trituration of the residue with diisopropyl ether gives 15.5 g (71% of theory) of 3-iodo-2-pyridinesulfonamide of melting point 247°–250 ° C. (dec.)

Example 3

3-(4,6-Dimethoxypyrimidin-2-yl)-1-(3-iodo-2-pyridylsulfonyl)urea 1.2 g (0.081 mol) of 1,8-diazabicyclo[5.4.0]undec-7-ene (DBU) are added to a suspension of 2.1 g (7.4 mmol) of 3-iodo-2-pyridinesulfonamide and 2.2 g (8.1 mmol) of N-(4,6-dimethoxypyrimidine-2-yl)phenyl carbamate in 30 ml of acetonitrile. The resulting solution is stirred at room temperature for 45 min and 20 ml of water are then added. The mixture is acidified to pH 4 using hydrochloric acid and the precipitated product is filtered off with suction. 3.2 g (93% of theory) of 3-(4,6-dimethoxypyrimidin-2-yl)-1-(3-iodo-2-pyridylsulfonyl)urea melting point 161°–162° C. (dec.) are obtained.

Example 4

3-Dimethylsulfamoyloxy-2-pyridinesulfonamide 107 ml (72 mmol) of a 5% strength sodium hypochlorite solution are added dropwise at 0° C. to a mixture of 5.7 g (17.6 mol) of 2-benzylthio-3-dimethylsulfamoyloxypyridine, 30 ml of dichloromethane, 15 ml of water and 8.5 ml of concentrated hydrochloric acid. The mixture is stirred at 0° C. for 30 min, extracted 3× using 20 ml of dichloromethane each time and the organic phase is dried using sodium sulfate. The solution thus obtained is cooled to −70° C. Ammonia is passed in at this temperature until the reaction mixture gives a distinctly alkaline reaction. After stirring at −70° C. for 3 hours, the mixture is allowed to come to room temperature and is washed with water. The organic phase is dried and evaporated. 3.0 g (61% of theory) of 3-dimethylsulfamoyloxy-oxy-2-pyridinesulfonamide are obtained;

NMR (CDCl$_3$): δ (ppm) = 3.06 (s, 6H, N(CH$_3$)$_2$), 5.80 (s, 2H, NH$_2$), 7.48 (dd, 1H), 7.98 (dd, 1H), 8.38 (dd, 1H).

Example 5

3-(4,6-Dimethoxypyrimidin-2-yl)-1-(3-dimethylsulfamoyloxy-2-pyridylsulfonyl)urea 1.9 g (12.7 mmol) of 1,8-diazabicyclo[5.4.0]undec-7-ene (DBU) are added to a suspension of 3.0 [lacuna] (10.6 mmol) of 3-dimethylsulfamoyloxy-2-pyridinesulfonamide and 3.4 g (12.7 mmol) of N-(4,6-dimethoxypyrimidin-2-yl)phenyl carbamate in 40 ml of acetonitrile. The resulting solution is stirred at room temperature for 1 h and 30 ml of water are then added. The mixture is acidified to pH 4 using hydrochloric acid and the precipitated product is filtered off with suction. After triturating with diethyl ether, 2.1 g (42% of theory) of 3-(4,6-dimethoxypyrimidin-2-yl)-1-(3-dimethylsulfamoyloxy-2-pyridylsulfonyl)urea of melting point 155°–157° C. are obtained.

Example 6

3-(4,6-Dimethoxy-1,3,5-triazin-2-yl)-1-(3-iodo-2-pyridylsulfonyl)urea 9.0 ml (18 mmol) of a 2M solution of trimethylaluminum in toluene are added dropwise at room temperature to 4.3 g (15 mmol) of 3-iodo-2-pyridinesulfonamide in 150 ml of dichloromethane. After evolution of gas has ceased, 3.85 [lacuna] (18 mmol) of methyl 4,6-dimethoxy-1,3,5-triazin-2-yl-carbamate in 20 ml of dichloromethane is added dropwise and the resulting solution is refluxed for 24 hours. The mixture is cooled and poured into 150 ml of ice-cold 1N hydrochloric acid. The organic phase is separated off and the aqueous phase is extracted 2× using dichloromethane. The organic phase is dried and evaporated. After triturating the crude product with diethyl ether, 3.1 g (44% of theory) of 3-(4,6-dimethoxy-1,3,5-triazin-2-yl)-1-(3-iodo-2-pyridylsulfonyl)urea of melting point 155° C. (dec.) are obtained.

The compounds in the following Tables 1 to 4 are obtained analogously to the processes of Examples 1–6.

TABLE 1

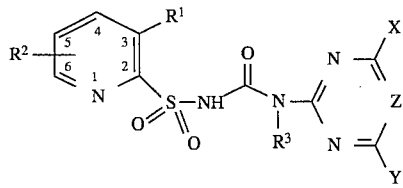

| Cpd. No. | R$^1$ | R$^2$ | R$^3$ | X | Y | Z | M.p. [°C.] |
|---|---|---|---|---|---|---|---|
| 1 | I | H | H | OCH$_3$ | OCH$_3$ | CH | 161–162 (D.) |
| 2 | " | H | CH$_3$ | OCH$_3$ | OCH$_3$ | CH | |
| 3 | " | H | CH$_3$ | OCH$_3$ | CH$_3$ | N | |
| 4 | " | H | H | CH$_3$ | CH$_3$ | CH | 186 (D.) |
| 5 | " | H | H | OCH$_3$ | CH$_3$ | CH | 177–178 |
| 6 | " | H | H | CH$_3$ | CH$_3$ | N | |
| 7 | " | H | H | OCH$_3$ | CH$_3$ | N | 156–157 (dec.) |
| 8 | " | H | H | OCH$_3$ | OCH$_3$ | N | 155 (dec.) |
| 9 | " | H | H | OCH$_3$ | Cl | CH | |
| 10 | " | H | H | OCF$_2$H | CH$_3$ | CH | |
| 11 | " | H | H | OCF$_2$H | OCF$_2$H | CH | |
| 12 | " | H | H | OCH$_3$ | Br | CH | |
| 13 | " | H | H | OCH$_3$ | OC$_2$H$_5$ | CH | |
| 14 | " | H | H | OCH$_3$ | SCH$_3$ | CH | |
| 15 | " | H | H | OCH$_3$ | OC$_2$H$_5$ | N | |
| 16 | " | H | H | OCH$_3$ | OC$_3$H$_7$ | CH | |
| 17 | " | H | H | OCH$_3$ | Cl | N | |
| 18 | " | H | H | Cl | OC$_2$H$_5$ | CH | |
| 19 | " | H | H | OC$_2$H$_5$ | OC$_2$H$_5$ | CH | |
| 20 | " | H | H | C$_2$H$_5$ | OCH$_3$ | CH | |
| 21 | " | H | H | CF$_3$ | OCH$_3$ | CH | |
| 22 | " | H | H | OCH$_2$CF$_3$ | CH$_3$ | CH | |
| 23 | " | H | H | OCH$_2$CF$_3$ | OCH$_3$ | CH | |
| 24 | " | H | H | OCH$_2$CF$_3$ | OCH$_2$CF$_3$ | CH | |
| 25 | " | H | H | OCH$_2$CF$_3$ | OCH$_3$ | N | |
| 26 | " | H | H | OCH$_3$ | CH(OCH$_3$)$_2$ | CH | |

TABLE 1-continued

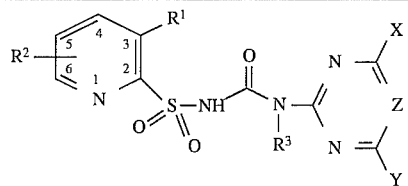

| Cpd. No. | R¹ | R² | R³ | X | Y | Z | M.p. [°C.] |
|---|---|---|---|---|---|---|---|
| 27 | " | 4-CH₃ | H | OCH₃ | OCH₃ | CH | |
| 28 | " | " | H | OCH₃ | CH₃ | CH | |
| 29 | " | " | H | OCH₃ | Cl | CH | |
| 30 | " | " | H | CH₃ | CH₃ | CH | |
| 31 | " | " | H | OCH₃ | OCH₃ | N | |
| 32 | " | " | H | OCH₃ | CH₃ | N | |
| 33 | " | " | H | OC₂H₅ | NHCH₃ | N | |
| 34 | " | " | CH₃ | OCH₃ | CH₃ | N | |
| 35 | " | 5-CH₃ | H | OCH₃ | OCH₃ | CH | |
| 36 | " | " | H | OCH₃ | CH₃ | CH | |
| 37 | " | " | H | OCH₃ | Cl | CH | |
| 38 | " | " | H | CH₃ | CH₃ | CH | |
| 39 | " | " | H | OCH₃ | OCH₃ | N | |
| 40 | " | " | H | OCH₃ | CH₃ | N | |
| 41 | " | " | H | OC₂H₅ | NHCH₃ | N | |
| 42 | " | " | CH₃ | OCH₃ | CH₃ | N | |
| 43 | " | 6-CH₃ | H | OCH₃ | OCH₃ | CH | |
| 44 | " | " | H | OCH₃ | CH₃ | CH | |
| 45 | " | " | H | OCH₃ | Cl | CH | |
| 46 | " | " | H | CH₃ | CH₃ | CH | |
| 47 | " | " | H | OCH₃ | OCH₃ | N | |
| 48 | " | " | H | OCH₃ | CH₃ | N | |
| 49 | " | " | H | OC₂H₅ | NHCH₃ | N | |
| 50 | " | " | CH₃ | OCH₃ | CH₃ | N | |
| 51 | " | 4-Cl | H | OCH₃ | OCH₃ | CH | |
| 52 | " | " | H | OCH₃ | CH₃ | CH | |
| 53 | " | " | H | OCH₃ | Cl | CH | |
| 54 | " | " | H | CH₃ | CH₃ | CH | |
| 55 | " | " | H | OCH₃ | OCH₃ | N | |
| 56 | " | " | H | OCH₃ | CH₃ | N | |
| 57 | " | " | H | OC₂H₅ | NHCH₃ | N | |
| 58 | 41 | " | CH₃ | OCH₃ | CH₃ | N | |
| 59 | " | 5-Cl | H | OCH₃ | OCH₃ | CH | |
| 60 | " | " | H | OCH₃ | CH₃ | CH | |
| 61 | " | " | H | OCH₃ | Cl | CH | |
| 62 | " | " | H | CH₃ | CH₃ | CH | |
| 63 | " | " | H | OCH₃ | OCH₃ | N | |
| 64 | " | " | H | OCH₃ | CH₃ | N | |
| 65 | " | " | H | OC₂H₅ | NHCH₃ | N | |
| 66 | " | " | CH₃ | OCH₃ | CH₃ | N | |
| 67 | " | 6-Cl | H | OCH₃ | OCH₃ | CH | |
| 68 | " | " | H | OCH₃ | CH₃ | CH | |
| 69 | " | " | H | OCH₃ | Cl | CH | |
| 70 | " | " | H | CH₃ | CH₃ | CH | |
| 71 | " | " | H | OCH₃ | OCH₃ | N | |
| 72 | " | " | H | OCH₃ | CH₃ | N | |
| 73 | " | " | H | OC₂H₅ | NHCH₃ | N | |
| 74 | " | " | CH₃ | OCH₃ | CH₃ | N | |
| 75 | " | 4-CF₃ | H | OCH₃ | OCH₃ | CH | |
| 76 | " | " | H | OCH₃ | CH₃ | CH | |
| 77 | " | " | H | OCH₃ | Cl | CH | |
| 78 | " | " | H | CH₃ | CH₃ | CH | |
| 79 | " | " | H | OCH₃ | OCH₃ | N | |
| 80 | " | " | H | OCH₃ | CH₃ | N | |
| 81 | " | 4-F | H | OC₂H₅ | NHCH₃ | N | |
| 82 | " | " | CH₃ | OCH₃ | CH₃ | N | |
| 83 | " | 5-CF₃ | H | OCH₃ | OCH₃ | CH | |
| 84 | " | " | H | OCH₃ | CH₃ | CH | |
| 85 | " | " | H | OCH₃ | Cl | CH | |
| 86 | " | " | H | CH₃ | CH₃ | CH | |
| 87 | " | " | H | OCH₃ | OCH₃ | N | |
| 88 | " | " | H | OCH₃ | CH₃ | N | |
| 89 | " | 5-F | H | OC₂H₅ | NHCH₃ | N | |
| 90 | " | " | CH₃ | OCH₃ | CH₃ | N | |
| 91 | " | 6-F | H | OCH₃ | OCH₃ | CH | |
| 92 | " | " | H | OCH₃ | CH₃ | CH | |
| 93 | " | " | H | OCH₃ | Cl | CH | |
| 94 | " | " | H | CH₃ | CH₃ | CH | |

TABLE 1-continued

| Cpd. No. | R¹ | R² | R³ | X | Y | Z | M.p. [°C.] |
|---|---|---|---|---|---|---|---|
| 95 | " | " | H | OCH₃ | OCH₃ | N | |
| 96 | " | " | H | OCH₃ | CH₃ | N | |
| 97 | " | " | H | OC₂H₅ | NHCH₃ | N | |
| 98 | " | " | CH₃ | OCH₃ | CH₃ | N | |
| 99 | " | 4-OCH₃ | H | OCH₃ | OCH₃ | CH | |
| 100 | " | " | H | OCH₃ | CH₃ | CH | |
| 101 | " | " | H | OCH₃ | Cl | CH | |
| 102 | " | " | H | CH₃ | CH₃ | CH | |
| 103 | " | " | H | OCH₃ | OCH₃ | N | |
| 104 | " | " | H | OCH₃ | CH₃ | N | |
| 105 | " | " | H | OC₂H₅ | NHCH₃ | N | |
| 106 | " | " | CH₂ | OCH₃ | CH₃ | N | |
| 107 | " | 5-OCH₃ | H | OCH₃ | OCH₃ | CH | |
| 108 | " | " | H | OCH₃ | CH₃ | CH | |
| 109 | " | " | H | OCH₃ | Cl | CH | |
| 110 | " | " | H | CH₃ | CH₃ | CH | |
| 111 | " | " | H | OCH₃ | OCH₃ | N | |
| 112 | " | " | H | OCH₃ | CH₃ | N | |
| 113 | " | " | H | OC₂H₅ | NHCH₃ | N | |
| 114 | " | " | CH₃ | OCH₃ | CH₃ | N | |
| 115 | " | 6-OCH₃ | H | OCH₃ | OCH₃ | CH | |
| 116 | " | " | H | OCH₃ | CH₃ | CH | |
| 117 | " | " | H | OCH₃ | Cl | CH | |
| 118 | " | " | H | CH₃ | CH₃ | CH | |
| 119 | " | " | H | OCH₃ | OCH₃ | N | |
| 120 | " | " | H | OCH₃ | CH₃ | N | |
| 121 | " | " | H | OC₂H₅ | NHCH₃ | N | |
| 122 | " | " | CH₃ | OCH₃ | CH₃ | N | |
| 123 | " | 6-C₂H₅ | H | OCH₃ | OCH₃ | CH | |
| 124 | " | 6-C₄H₃ | H | OCH₃ | OCH₃ | CH | |
| 126 | " | 6-OC₂H₅ | H | OCH₃ | OCH₃ | CH | |
| 127 | " | 6-OCH₂CF₃ | H | OCH₃ | OCH₃ | CH | |
| 128 | " | 6-SCH₃ | H | OCH₃ | OCH₃ | CH | |
| 129 | " | 6-SO₂CH₃ | H | OCH₃ | OCH₃ | CH | |
| 130 | " | 6-NO₂ | H | OCH₃ | OCH₃ | CH | |
| 131 | " | 6-CO₂CH₃ | H | OCH₃ | OCH₃ | CH | |
| 132 | " | 6-Br | H | OCH₃ | OCH₃ | CH | |
| 133 | " | 6-CF₃ | H | OCH₃ | OCH₃ | CH | |
| 134 | " | 6-OCF₃ | H | OCH₃ | OCH₃ | CH | |
| 135 | " | 6-OCF₂H | H | OCH₃ | OCH₃ | CH | |
| 136 | —OSO₂N(CH₃)₂ | H | H | OCH₃ | OCH₃ | CH | 155–157 |
| 137 | " | H | CH₃ | OCH₃ | OCH₃ | CH | |
| 138 | " | H | CH₃ | OCH₃ | CH₃ | N | |
| 139 | " | H | H | CH₃ | CH₃ | CH | |
| 140 | " | H | H | OCH₃ | CH₃ | CH | |
| 141 | " | H | H | CH₃ | CH₃ | N | |
| 142 | " | H | H | OCH₃ | CH₃ | N | 137–138 (dec.) |
| 143 | " | H | H | OCH₃ | OCH₃ | N | |
| 144 | " | H | H | OCH₃ | Cl | CH | |
| 145 | " | H | H | OCF₂H | CH₃ | CH | |
| 146 | " | H | H | OCF₂H | OCF₂H | CH | |
| 147 | " | H | H | OCH₃ | Br | CH | |
| 148 | " | H | H | OCH₃ | OC₂H₅ | CH | |
| 149 | " | H | H | OCH₃ | SCH₃ | CH | |
| 150 | " | H | H | OCH₃ | OC₂H₅ | N | |
| 151 | " | H | H | OCH₃ | OC₃H₇ | CH | |
| 152 | " | H | H | OCH₃ | Cl | N | |
| 153 | " | H | H | Cl | OC₂H | CH | |
| 154 | " | H | H | OC₂H₅ | OC₂H | CH | |
| 155 | " | H | H | C₂H₅ | OCH₃ | CH | |
| 156 | " | H | H | CF₃ | OCH₃ | CH | |
| 157 | " | H | H | OCH₂CF₃ | CH₃ | CH | |
| 158 | " | H | H | OCH₂CF₃ | OCH₃ | CH | |
| 159 | " | H | H | OCH₂CF₃ | OCH₂CF₃ | CH | |
| 160 | " | H | H | OCH₂CF₃ | OCH₃ | N | |
| 161 | " | H | H | OCH₃ | CH(OCH₃)₂ | CH | |
| 162 | " | 4-CH₃ | H | OCH₃ | OCH₃ | CH | |
| 163 | " | " | H | OCH₃ | CH₃ | CH | |

TABLE 1-continued

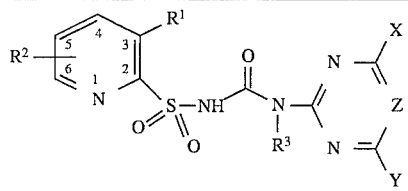

| Cpd. No. | R¹ | R² | R³ | X | Y | Z | M.p. [°C.] |
|---|---|---|---|---|---|---|---|
| 164 | " | " | H | OCH₃ | Cl | CH | |
| 165 | " | " | H | CH₃ | CH₃ | CH | |
| 166 | " | " | H | OCH₃ | OCH₃ | N | |
| 167 | " | " | H | OCH₃ | CH₃ | N | |
| 168 | " | " | H | OC₂H₅ | NHCH₃ | N | |
| 169 | " | " | CH₃ | OCH₃ | CH₃ | N | |
| 170 | " | 5-CH₃ | H | OCH₃ | OCH₃ | CH | |
| 171 | " | " | H | OCH₃ | CH₃ | CH | |
| 172 | " | " | H | OCH₃ | Cl | CH | |
| 173 | " | " | H | CH₃ | CH₃ | CH | |
| 174 | " | " | H | OCH₃ | OCH₃ | N | |
| 175 | " | " | H | OCH₃ | CH₃ | N | |
| 176 | " | " | H | OC₂H₅ | NHCH₃ | N | |
| 177 | " | " | CH₃ | OCH₃ | CH₃ | N | |
| 178 | " | 6-CH₃ | H | OCH₃ | OCH₃ | CH | |
| 179 | " | " | H | OCH₃ | CH₃ | CH | |
| 180 | " | " | H | OCH₃ | Cl | CH | |
| 181 | " | " | H | CH₃ | CH₃ | CH | |
| 182 | " | " | H | OCH₃ | OCH₃ | N | |
| 183 | " | " | H | OCH₃ | CH₃ | N | |
| 184 | " | " | H | OC₂H₅ | NHCH₃ | N | |
| 185 | " | " | CH₃ | OCH₃ | CH₃ | N | |
| 186 | " | 4-Cl | H | OCH₃ | OCH₃ | CH | |
| 187 | " | " | H | OCH₃ | CH₃ | CH | |
| 188 | " | " | H | OCH₃ | Cl | CH | |
| 189 | " | " | H | CH₃ | CH₃ | CH | |
| 190 | " | " | H | OCH₃ | OCH₃ | N | |
| 191 | " | " | H | OCH₃ | CH₃ | N | |
| 192 | " | " | H | OC₂H₅ | NHCH₃ | N | |
| 193 | " | " | CH₃ | OCH₃ | CH₃ | N | |
| 194 | " | 5-Cl | H | OCH₃ | OCH₃ | CH | |
| 195 | " | " | H | OCH₃ | CH₃ | CH | |
| 196 | " | " | H | OCH₃ | Cl | CH | |
| 197 | " | " | H | CH₃ | CH₃ | CH | |
| 198 | " | " | H | OCH₃ | OCH₃ | N | |
| 199 | " | " | H | OCH₃ | CH₃ | N | |
| 200 | " | " | H | OC₂H₅ | NHCH₃ | N | |
| 201 | " | " | CH₃ | OCH₃ | CH₃ | N | |
| 202 | " | 6-Cl | H | OCH₃ | OCH₃ | CH | |
| 203 | " | " | H | OCH₃ | CH₃ | CH | |
| 204 | " | " | H | OCH₃ | Cl | CH | |
| 205 | " | " | H | CH₃ | CH₃ | CH | |
| 206 | " | " | H | OCH₃ | OCH₃ | N | |
| 207 | " | " | H | OCH₃ | CH₃ | N | |
| 208 | " | " | H | OC₂H₅ | NHCH₃ | N | |
| 209 | " | " | CH₃ | OCH₃ | CH₃ | N | |
| 210 | " | 4-F | H | OCH₃ | OCH₃ | CH | |
| 211 | " | " | H | OCH₃ | CH₃ | CH | |
| 212 | " | " | H | OCH₃ | Cl | CH | |
| 213 | " | " | H | CH₃ | CH₃ | CH | |
| 214 | " | " | H | OCH₃ | OCH₃ | N | |
| 215 | " | " | H | OCH₃ | CH₃ | N | |
| 216 | " | " | H | OC₂H₅ | NHCH₃ | N | |
| 217 | " | " | CH₃ | OCH₃ | CH₃ | N | |
| 218 | " | 5-F | H | OCH₃ | OCH₃ | CH | |
| 219 | " | " | H | OCH₃ | CH₃ | CH | |
| 220 | " | " | H | OCH₃ | Cl | CH | |
| 221 | " | " | H | CH₃ | CH₃ | CH | |
| 222 | " | " | H | OCH₃ | OCH₃ | N | |
| 223 | " | " | H | OCH₃ | CH₃ | N | |
| 224 | " | " | H | OC₂H₅ | NHCH₃ | N | |
| 225 | " | " | CH₃ | OCH₃ | CH₃ | N | |
| 226 | " | 6-F | H | OCH₃ | OCH₃ | CH | |
| 227 | " | " | H | OCH₃ | CH₃ | CH | |
| 228 | " | " | H | OCH₃ | Cl | CH | |
| 229 | " | " | H | CH₃ | CH₃ | CH | |
| 230 | " | " | H | OCH₃ | OCH₃ | N | |
| 231 | " | " | H | OCH₃ | CH₃ | N | |

TABLE 1-continued

| Cpd. No. | R¹ | R² | R³ | X | Y | Z | M.p. [°C.] |
|---|---|---|---|---|---|---|---|
| 232 | " | " | H | OC$_2$H$_5$ | NHCH$_3$ | N | |
| 233 | " | " | CH$_3$ | OCH$_3$ | CH$_3$ | N | |
| 234 | " | 4-OCH$_2$ | H | OCH$_3$ | OCH$_3$ | CH | |
| 235 | " | " | H | OCH$_3$ | CH$_3$ | CH | |
| 236 | " | " | H | OCH$_3$ | Cl | CH | |
| 237 | " | " | H | CH$_3$ | CH$_3$ | CH | |
| 238 | " | " | H | OCH$_3$ | OCH$_3$ | N | |
| 239 | " | " | H | OCH$_3$ | CH$_3$ | N | |
| 240 | " | " | H | OC$_2$H$_5$ | NHCH$_3$ | N | |
| 241 | " | " | CH$_3$ | OCH$_3$ | CH$_3$ | N | |
| 242 | " | 5-OCH$_3$ | H | OCH$_3$ | OCH$_3$ | CH | |
| 243 | " | " | H | OCH$_3$ | CH$_3$ | CH | |
| 244 | " | " | H | OCH$_3$ | Cl | CH | |
| 245 | " | " | H | CH$_3$ | CH$_3$ | CH | |
| 246 | " | " | H | OCH$_3$ | OCH$_3$ | N | |
| 247 | " | " | H | OCH$_3$ | CH$_3$ | N | |
| 248 | " | " | H | OC$_2$H$_5$ | NHCH$_3$ | N | |
| 249 | " | " | CH$_3$ | OCH$_3$ | CH$_3$ | N | |
| 250 | " | 6-OCH$_3$ | H | OCH$_3$ | OCH$_3$ | CH | |
| 251 | " | " | H | OCH$_3$ | CH$_3$ | CH | |
| 252 | " | " | H | OCH$_3$ | Cl | CH | |
| 253 | " | " | H | CH$_3$ | CH$_3$ | CH | |
| 254 | " | " | H | OCH$_3$ | OCH$_3$ | N | |
| 255 | " | " | H | OCH$_3$ | CH$_3$ | N | |
| 256 | " | " | H | OC$_2$H$_5$ | NHCH$_3$ | N | |
| 257 | " | " | CH$_3$ | OCH$_3$ | CH$_3$ | N | |
| 258 | " | 6-C$_2$H$_5$ | H | OCH$_3$ | OCH$_3$ | CH | |
| 259 | " | 6-C$_4$H$_9$ | H | OCH$_3$ | OCH$_3$ | CH | |
| 260 | " | 6-OC$_2$H$_5$ | H | OCH$_3$ | OCH$_3$ | CH | |
| 261 | " | 6-OCH$_2$CF$_3$ | H | OCH$_3$ | OCH$_3$ | CH | |
| 262 | " | 6-SCH$_3$ | H | OCH$_3$ | OCH$_3$ | CH | |
| 263 | " | 6-SO$_2$CH$_3$ | H | OCH$_3$ | OCH$_3$ | CH | |
| 264 | " | 6-NO$_2$ | H | OCH$_3$ | OCH$_3$ | CH | |
| 265 | " | 6-CO$_2$CH$_3$ | H | OCH$_3$ | OCH$_3$ | CH | |
| 266 | " | 6-Br | H | OCH$_3$ | OCH$_3$ | CH | |
| 267 | " | 6-CF$_2$ | H | OCH$_3$ | OCH$_3$ | CH | |
| 268 | " | 6-OCF$_2$ | H | OCH$_3$ | OCH$_3$ | CH | |
| 269 | " | 6-OCF$_2$H | H | OCH$_3$ | OCH$_3$ | CH | |
| 270 | —OSO$_2$N(CH$_3$)(C$_2$H$_5$) | H | H | OCH$_3$ | OCH$_3$ | CH | |
| 271 | " | H | H | OCH$_3$ | CH$_3$ | CH | |
| 272 | " | H | H | OCH$_3$ | Cl | CH | |
| 273 | " | H | H | CH$_3$ | CH$_3$ | CH | |
| 274 | " | H | H | OCH$_3$ | OCH$_3$ | N | |
| 275 | " | H | H | OCH$_3$ | CH$_3$ | N | |
| 276 | " | H | H | OC$_2$H$_5$ | NHCH$_3$ | N | |
| 277 | " | H | CH$_3$ | OCH$_3$ | CH$_3$ | N | |
| 278 | " | 4-CH$_3$ | H | OCH$_3$ | OCH$_3$ | CH | |
| 279 | " | 4-Cl | H | OCH$_3$ | OCH$_3$ | CH | |
| 280 | " | 6-CH$_3$ | H | OCH$_3$ | OCH$_3$ | CH | |
| 281 | " | 6-OCH$_3$ | H | OCH$_3$ | OCH$_3$ | CH | |
| 282 | " | 6-Cl | H | OCH$_3$ | OCH$_3$ | CH | |
| 283 | —OSO$_2$N(CH$_3$)OCH$_3$ | H | H | OCH$_3$ | OCH$_3$ | CH | |
| 284 | —OSO$_3$N(CH$_3$)(C$_3$H$_7$) | H | H | OCH$_3$ | OCH$_3$ | CH | |
| 285 | " | H | H | OCH$_3$ | CH$_3$ | CH | |
| 286 | " | H | H | OCH$_3$ | Cl | CH | |
| 287 | " | H | H | CH$_3$ | CH$_3$ | CH | |

TABLE 1-continued

| Cpd. No. | R¹ | R² | R³ | X | Y | Z | M.p. [°C.] |
|---|---|---|---|---|---|---|---|
| 288 | " | H | H | OCH₃ | OCH₃ | N | |
| 289 | " | H | H | OCH₃ | CH₃ | N | |
| 290 | " | H | H | OC₂H₅ | NHCH₃ | N | |
| 291 | " | H | CH₃ | OCH₃ | CH₃ | N | |
| 292 | " | 4-CH₃ | H | OCH₃ | OCH₃ | CH | |
| 293 | " | 4-Cl | H | OCH₃ | OCH₃ | CH | |
| 294 | " | 6-CH₃ | H | OCH₃ | OCH₃ | CH | |
| 295 | " | 6-OCH₃ | H | OCH₃ | OCH₃ | CH | |
| 296 | " | 6-Cl | H | OCH₃ | OCH₃ | CH | |
| 297 | —OSO₂N(Allyl)₂ | H | H | OCH₃ | OCH₃ | CH | |
| 298 | —OSO₂N(C₂H₅)₂ | H | H | OCH₃ | OCH₃ | CH | 157–158 |
| 299 | " | H | H | OCH₃ | CH₃ | CH | 151–153 (D.) |
| 300 | " | H | H | OCH₃ | Cl | CH | |
| 301 | " | H | H | CH₃ | CH₃ | CH | 159–160 (D.) |
| 302 | " | H | H | OCH₃ | OCH₃ | N | |
| 303 | " | H | H | OCH₃ | CH₃ | N | 146–149 (D.) |
| 304 | " | H | H | OC₂H₅ | NHCH₃ | N | |
| 305 | " | H | CH₃ | OCH₃ | CH₃ | N | |
| 306 | " | 4-CH₃ | H | OCH₃ | OCH₃ | CH | |
| 307 | " | 4-Cl | H | OCH₃ | OCH₃ | CH | |
| 308 | " | 6-CH₃ | H | OCH₃ | OCH₃ | CH | |
| 309 | " | 6-OCH₃ | H | OCH₃ | OCH₃ | CH | |
| 310 | " | 6-Cl | H | OCH₃ | OCH₃ | CH | |
| 311 | " | 6-F | H | OCH₃ | OCH₃ | CH | |
| 312 | —OSO₂N(pyrrolidinyl) | H | H | OCH₃ | OCH₃ | CH | 158–159 |
| 313 | " | H | H | OCH₃ | CH₃ | CH | 170–171 |
| 314 | " | H | H | OCH₃ | Cl | CH | |
| 315 | " | H | H | CH₃ | CH₃ | CH | 169–170 |
| 316 | " | H | H | OCH₃ | OCH₃ | N | |
| 317 | " | H | H | OCH₃ | CH₃ | N | 155 |
| 318 | " | H | H | OC₂H₅ | NHCH₃ | N | |
| 319 | " | H | CH₃ | OCH₃ | CH₃ | N | |
| 320 | " | 4-CH₃ | H | OCH₃ | OCH₃ | CH | |
| 321 | " | 4-Cl | H | OCH₃ | OCH₃ | CH | |
| 322 | " | 6-CH₃ | H | OCH₃ | OCH₃ | CH | |
| 323 | " | 6-OCH₃ | H | OCH₃ | OCH₃ | CH | |
| 324 | " | 6-Cl | H | OCH₃ | OCH₃ | CH | |
| 325 | " | 6-F | H | OCH₃ | OCH₃ | CH | |
| 326 | —OSO₂N(piperidinyl) | H | H | OCH₃ | OCH₃ | CH | 173–174 (D.) |
| 327 | " | H | H | OCH₃ | CH₃ | CH | |
| 328 | " | H | H | OCH₃ | Cl | CH | |
| 329 | " | H | H | CH₃ | CH₃ | CH | 185–186 (D.) |
| 330 | " | H | H | OCH₃ | OCH₃ | N | |
| 331 | " | H | H | OCH₃ | CH₃ | N | |
| 332 | " | H | H | OC₂H₅ | NHCH₃ | N | |
| 333 | " | H | CH₃ | OCH₃ | CH₃ | N | |
| 334 | " | 4-CH₃ | H | OCH₃ | OCH₃ | CH | |
| 335 | " | 4-Cl | H | OCH₃ | OCH₃ | CH | |
| 336 | " | 6-CH₃ | H | OCH₃ | OCH₃ | CH | |
| 337 | " | 6-OCH₃ | H | OCH₃ | OCH₃ | CH | |
| 338 | " | 6-Cl | H | OCH₃ | OCH₃ | CH | |
| 339 | " | 6-F | H | OCH₃ | OCH₃ | CH | |

TABLE 1-continued

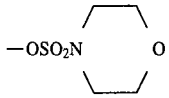

| Cpd. No. | R¹ | R² | R³ | X | Y | Z | M.p. [°C.] |
|---|---|---|---|---|---|---|---|
| 340 | —OSO₂N⟨O⟩ | H | H | OCH₃ | OCH₃ | CH | 141–142 (D.) |
| 341 | " | H | H | OCH₃ | CH₃ | CH | |
| 342 | " | H | H | OCH₃ | Cl | CH | |
| 343 | " | H | H | CH₃ | CH₃ | CH | |
| 344 | " | H | H | OCH₃ | OCH₃ | N | |
| 345 | " | H | H | OCH₃ | CH₃ | N | |
| 346 | " | H | H | OC₂H₅ | NHCH₃ | N | |
| 347 | " | H | CH₃ | OCH₃ | CH₃ | N | |
| 348 | " | 4-CH₃ | H | OCH₃ | OCH₃ | CH | |
| 349 | " | 4-Cl | H | OCH₃ | OCH₃ | CH | |
| 350 | " | 6-CH₃ | H | OCH₃ | OCH₃ | CH | |
| 351 | " | 6-OCH₃ | H | OCH₃ | OCH₃ | CH | |
| 352 | " | 6-Cl | H | OCH₃ | OCH₃ | CH | |
| 353 | " | 6-F | H | OCH₃ | OCH₃ | CH | |
| 354 | —NHSO₂CH₃ | H | H | OCH₃ | OCH₃ | CH | 191–192 (D.) |
| 355 | " | H | H | OCH₃ | CH₃ | CH | |
| 356 | " | H | H | OCH₃ | Cl | CH | |
| 357 | " | H | H | CH₃ | CH₃ | CH | |
| 358 | " | H | H | OCH₃ | OCH₃ | N | |
| 359 | " | H | H | OCH₃ | CH₃ | N | |
| 360 | " | H | H | OC₂H₅ | NHCH₃ | N | |
| 361 | " | H | CH₃ | OCH₃ | CH₃ | N | |
| 362 | " | 4-CH₃ | H | OCH₃ | OCH₃ | CH | |
| 363 | " | 4-Cl | H | OCH₃ | OCH₃ | CH | |
| 364 | " | 6-CH₃ | H | OCH₃ | OCH₃ | CH | |
| 365 | " | 6-OCH₃ | H | OCH₃ | OCH₃ | CH | |
| 366 | " | 6-Cl | H | OCH₃ | OCH₃ | CH | |
| 367 | " | 6-F | H | OCH₃ | OCH₃ | CH | |
| 368 | —NHSO₂C₂H₅ | H | H | OCH₃ | OCH₃ | CH | |
| 369 | " | H | H | OCH₃ | CH₃ | CH | |
| 370 | " | H | H | OCH₃ | Cl | CH | |
| 371 | " | H | H | CH₃ | CH₃ | CH | |
| 372 | " | H | H | OCH₃ | OCH₃ | N | |
| 373 | " | H | H | OCH₃ | CH₃ | N | |
| 374 | " | H | H | OC₂H₅ | NHCH₃ | N | |
| 375 | " | H | CH₃ | OCH₃ | CH₃ | N | |
| 376 | " | 4-CH₃ | H | OCH₃ | OCH₃ | CH | |
| 377 | " | 4-Cl | H | OCH₃ | OCH₃ | CH | |
| 378 | " | 6-CH₃ | H | OCH₃ | OCH₃ | CH | |
| 379 | " | 6-OCH₃ | H | OCH₃ | OCH₃ | CH | |
| 380 | " | 6-Cl | H | OCH₃ | OCH₃ | CH | |
| 381 | " | 6-F | H | OCH₃ | OCH₃ | CH | |
| 382 | —NHSO₂C₃H₇ | H | H | OCH₃ | OCH₃ | CH | |
| 383 | " | H | H | OCH₃ | CH₃ | CH | |
| 384 | " | H | H | OCH₃ | Cl | CH | |
| 385 | " | H | H | CH₃ | CH₃ | CH | |
| 386 | " | H | H | OCH₃ | OCH₃ | N | |
| 387 | " | H | H | OCH₃ | CH₃ | N | |
| 388 | " | H | H | OC₂H₅ | NHCH₃ | N | |
| 389 | " | H | CH₃ | OCH₃ | CH₃ | N | |
| 390 | " | 4-CH₃ | H | OCH₃ | OCH₃ | CH | |
| 391 | " | 4-Cl | H | OCH₃ | OCH₃ | CH | |
| 392 | " | 6-CH₃ | H | OCH₃ | OCH₃ | CH | |
| 393 | " | 6-OCH₃ | H | OCH₃ | OCH₃ | CH | |
| 394 | " | 6-Cl | H | OCH₃ | OCH₃ | CH | |
| 395 | " | 6-F | H | OCH₃ | OCH₃ | CH | |
| 396 | —NHSO₂C₃H₅ | H | H | OCH₃ | OCH₃ | CH | |
| 397 | " | H | H | OCH₃ | CH₃ | CH | |
| 398 | " | H | H | OCH₃ | Cl | CH | |
| 399 | " | H | H | CH₃ | CH₃ | CH | |
| 401 | " | H | H | OCH₃ | OCH₃ | N | |
| 402 | " | H | H | OCH₃ | CH₃ | N | |

TABLE 1-continued

| Cpd. No. | R¹ | R² | R³ | X | Y | Z | M.p. [°C.] |
|---|---|---|---|---|---|---|---|
| 403 | " | H | H | OC₂H₅ | NHCH₃ | N | |
| 404 | " | H | CH₃ | OCH₃ | CH₃ | N | |
| 405 | " | 4-CH₃ | H | OCH₃ | OCH₃ | CH | |
| 406 | " | 4-Cl | H | OCH₃ | OCH₃ | CH | |
| 407 | " | 6-CH₃ | H | OCH₃ | OCH₃ | CH | |
| 408 | " | 6-OCH₃ | H | OCH₃ | OCH₃ | CH | |
| 409 | " | 6-Cl | H | OCH₃ | OCH₃ | CH | |
| 410 | " | 6-F | H | OCH₃ | OCH₃ | CH | |
| 411 | —N(SO₂CH₃)₂ | H | H | OCH₃ | OCH₃ | CH | 219–220 (D.) |
| 412 | " | H | H | OCH₃ | CH₃ | CH | |
| 413 | " | H | H | OCH₃ | Cl | CH | |
| 414 | " | H | H | CH₃ | CH₃ | CH | |
| 415 | " | H | H | OCH₃ | OCH₃ | N | |
| 416 | " | H | H | OCH₃ | CH₃ | N | |
| 417 | " | H | H | OC₂H₅ | NHCH₃ | N | |
| 418 | " | H | CH₃ | OCH₃ | CH₃ | N | |
| 419 | " | 4-CH₃ | H | OCH₃ | OCH₃ | CH | |
| 420 | " | 4-Cl | H | OCH₃ | OCH₃ | CH | |
| 421 | " | 6-CH₃ | H | OCH₃ | OCH₃ | CH | |
| 422 | " | 6-OCH₃ | H | OCH₃ | OCH₃ | CH | |
| 423 | " | 6-Cl | H | OCH₃ | OCH₃ | CH | |
| 424 | " | 6-F | H | OCH₃ | OCH₃ | CH | |
| 425 | —N(SO₂C₂H₅)₂ | H | H | OCH₃ | OCH₃ | CH | |
| 426 | " | H | H | OCH₃ | CH₃ | CH | |
| 427 | " | H | H | OCH₃ | Cl | CH | |
| 428 | " | H | H | CH₃ | CH₃ | CH | |
| 429 | " | H | H | OCH₃ | OCH₃ | N | |
| 430 | " | H | H | OCH₃ | CH₃ | N | |
| 431 | " | H | H | OC₂H₅ | NHCH₃ | N | |
| 432 | " | H | CH₃ | OCH₃ | CH₃ | N | |
| 433 | " | 4-CH₃ | H | OCH₃ | OCH₃ | CH | |
| 434 | " | 4-Cl | H | OCH₃ | OCH₃ | CH | |
| 435 | " | 6-CH₃ | H | OCH₃ | OCH₃ | CH | |
| 436 | " | 6-OCH₃ | H | OCH₃ | OCH₃ | CH | |
| 437 | " | 6-Cl | H | CH₃ | OCH₃ | CH | |
| 438 | " | 6-F | H | OCH₃ | OCH₃ | CH | |
| 439 | —N(CH₃)SO₂CH₃ | H | H | OCH₃ | OCH₃ | CH | 177–178 |
| 440 | " | H | H | OCH₃ | OCH₃ | CH | 152–153 |
| 441 | " | H | CH₃ | OCH₃ | CH₃ | N | |
| 442 | " | H | H | CH₃ | CH₃ | CH | 185–186 (D.) |
| 443 | " | H | H | OCH₃ | CH₃ | CH | 169–170 (D.) |
| 444 | " | H | H | CH₃ | OC₂H₅ | CH | |
| 445 | " | H | H | OCH₃ | CH₃ | N | 158–159 (D.) |
| 446 | " | H | H | OCH₃ | OCH₃ | N | 173–174 (D.) |
| 447 | " | H | H | OCH₃ | Cl | CH | 167–169 |
| 448 | " | H | H | OCF₂H | CH₃ | CH | |
| 449 | " | H | H | OCF₂H | OCF₂H | CH | |
| 450 | " | H | H | OCH₃ | Br | CH | |
| 451 | " | H | H | OCH₃ | OC₂H₅ | CH | |
| 452 | " | H | H | OCH₃ | SCH₃ | CH | |
| 453 | " | H | H | OCH₃ | OC₂H₅ | N | |
| 454 | " | H | H | OCH₃ | OC₃H₇ | CH | |
| 455 | " | H | H | CH₃ | Cl | CH | 168–169 (D.) |
| 456 | " | H | H | Cl | OC₂H₅ | CH | |
| 457 | " | H | H | OC₂H₅ | OC₂H₅ | CH | |
| 458 | " | H | H | C₂H₅ | OCH₃ | CH | |
| 459 | " | H | H | CF₃ | OCH₃ | CH | |
| 460 | " | H | H | OCH₂CF₃ | CH₃ | CH | |
| 461 | " | H | H | OCH₂CF₃ | OCH₃ | CH | |
| 462 | " | H | H | OCH₂CF₃ | OCH₂CF₃ | CH | |
| 463 | " | H | H | OCH₂CF₃ | OCH₃ | N | |
| 464 | " | H | H | OCH₃ | CH(OCH₃)₂ | CH | |
| 465 | " | 4-CH₃ | H | OCH₃ | OCH₃ | CH | |
| 466 | " | " | H | OCH₃ | CH₃ | CH | |
| 467 | " | " | H | OCH₃ | Cl | CH | |
| 468 | " | " | H | CH₃ | CH₃ | CH | |
| 469 | " | " | H | OCH₃ | OCH₃ | N | |
| 470 | " | " | H | OCH₃ | CH₃ | N | |

TABLE 1-continued

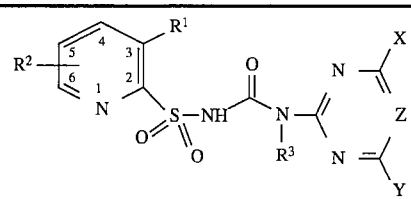

| Cpd. No. | R¹ | R² | R³ | X | Y | Z | M.p. [°C.] |
|---|---|---|---|---|---|---|---|
| 471 | " | " | H | OC₂H₅ | NHCH₃ | N | |
| 472 | " | " | CH₃ | OCH₃ | OCH₃ | CH | |
| 473 | " | 5-CH₃ | H | OCH₃ | OCH₃ | CH | |
| 474 | " | " | H | OCH₃ | CH₃ | CH | |
| 475 | " | " | H | OCH₃ | Cl | CH | |
| 476 | " | " | H | CH₃ | CH₃ | CH | |
| 477 | " | " | H | OCH₃ | OCH₃ | N | |
| 478 | " | " | H | OCH₃ | CH₃ | N | |
| 479 | " | " | H | OC₂H₅ | NHCH₃ | N | |
| 480 | " | " | CH₃ | OCH₃ | OCH₃ | CH | |
| 481 | " | 6-CH₃ | H | OCH₃ | OCH₃ | CH | 185 |
| 482 | " | " | H | OCH₃ | CH₃ | CH | |
| 483 | " | " | H | OCH₃ | Cl | CH | |
| 484 | " | " | H | CH₃ | CH₃ | CH | |
| 485 | " | " | H | OCH₃ | OCH₃ | N | |
| 486 | " | " | H | OCH₃ | CH₃ | N | |
| 487 | " | " | H | OC₂H₅ | NHCH₃ | N | |
| 488 | " | " | CH₃ | OCH₃ | OCH₃ | CH | |
| 489 | " | 4-Cl | H | OCH₃ | OCH₃ | CH | |
| 490 | " | " | H | OCH₃ | CH₃ | CH | |
| 491 | " | " | H | OCH₃ | Cl | CH | |
| 492 | " | " | H | CH₃ | CH₃ | CH | |
| 493 | " | " | H | OCH₃ | OCH₃ | N | |
| 494 | " | " | H | OCH₃ | CH₃ | N | |
| 495 | " | " | H | OC₂H₅ | NHCH₃ | N | |
| 496 | " | " | CH₃ | OCH₃ | OCH₃ | CH | |
| 497 | " | 5-Cl | H | OCH₃ | OCH₃ | CH | |
| 498 | " | " | H | OCH₃ | CH₃ | CH | |
| 499 | " | " | H | OCH₃ | Cl | CH | |
| 500 | " | " | H | CH₃ | CH₃ | CH | |
| 501 | " | " | H | OCH₃ | OCH₃ | N | |
| 502 | " | " | H | OCH₃ | CH₃ | N | |
| 503 | " | " | H | OC₂H₅ | NHCH₃ | N | |
| 504 | " | " | CH₃ | OCH₃ | OCH₃ | CH | |
| 505 | " | 6-Cl | H | OCH₃ | OCH₃ | CH | |
| 506 | " | " | H | OCH₃ | CH₃ | CH | |
| 507 | " | " | H | OCH₃ | Cl | CH | |
| 508 | " | " | H | CH₃ | CH₃ | CH | |
| 509 | " | " | H | OCH₃ | OCH₃ | N | |
| 510 | " | " | H | OCH₃ | CH₃ | N | |
| 511 | " | " | H | OC₂H₅ | NHCH₃ | N | |
| 512 | " | " | CH₃ | OCH₃ | OCH₃ | CH | |
| 513 | " | 4-CF₃ | H | OCH₃ | OCH₃ | CH | |
| 514 | " | " | H | OCH₃ | CH₃ | CH | |
| 515 | " | " | H | OCH₃ | Cl | CH | |
| 516 | " | " | H | CH₃ | CH₃ | CH | |
| 517 | " | " | H | OCH₃ | OCH₃ | N | |
| 518 | " | " | H | OCH₃ | CH₃ | N | |
| 519 | " | 4-F | H | OC₂H₅ | NHCH₃ | N | |
| 520 | " | " | CH₃ | OCH₃ | OCH₃ | CH | |
| 521 | " | 5-CF₃ | H | OCH₃ | OCH₃ | CH | |
| 522 | " | " | H | OCH₃ | CH₃ | CH | |
| 523 | " | " | H | OCH₃ | Cl | CH | |
| 524 | " | " | H | CH₃ | CH₃ | CH | |
| 525 | " | " | H | OCH₃ | OCH₃ | N | |
| 526 | " | " | H | OCH₃ | CH₃ | N | |
| 527 | " | 5-F | H | OC₂H₅ | NHCH₃ | N | |
| 528 | " | " | CH₃ | OCH₃ | OCH₃ | CH | |
| 529 | " | 6-F | H | OCH₃ | OCH₃ | CH | |
| 530 | " | " | H | OCH₃ | CH₃ | CH | |
| 531 | " | " | H | OCH₃ | Cl | CH | |
| 532 | " | " | H | CH₃ | CH₃ | CH | |
| 533 | " | " | H | OCH₃ | OCH₃ | N | |
| 534 | " | " | H | OCH₃ | CH₃ | N | |
| 535 | " | " | H | OC₂H₅ | NHCH₃ | N | |
| 536 | " | " | CH₃ | OCH₃ | OCH₃ | CH | |
| 537 | " | 4-OCH₃ | H | OCH₃ | OCH₃ | CH | |
| 538 | " | " | H | OCH₃ | CH₃ | CH | |

TABLE 1-continued

| Cpd. No. | R¹ | R² | R³ | X | Y | Z | M.p. [°C.] |
|---|---|---|---|---|---|---|---|
| 539 | " | " | H | OCH₃ | Cl | CH | |
| 540 | " | " | H | CH₃ | CH₃ | CH | |
| 541 | " | " | H | OCH₃ | OCH₃ | N | |
| 542 | " | " | H | OCH₃ | CH₃ | N | |
| 543 | " | " | H | OC₂H₅ | NHCH₃ | N | |
| 544 | " | " | CH₃ | OCH₃ | OCH₃ | CH | |
| 545 | " | 5-OCH₃ | H | OCH₃ | OCH₃ | CH | |
| 546 | " | " | H | OCH₃ | CH₃ | CH | |
| 547 | " | " | H | OCH₃ | Cl | CH | |
| 548 | " | " | H | CH₃ | CH₃ | CH | |
| 549 | " | " | H | OCH₃ | OCH₃ | N | |
| 550 | " | " | H | OCH₃ | CH₃ | N | |
| 551 | " | " | H | OC₂H₅ | NHCH₃ | N | |
| 552 | " | " | CH₃ | OCH₃ | OCH₃ | CH | |
| 553 | " | 6-OCH₃ | H | OCH₃ | OCH₃ | CH | |
| 554 | " | " | H | OCH₃ | CH₃ | CH | |
| 555 | " | " | H | OCH₃ | Cl | CH | |
| 556 | " | " | H | CH₃ | CH₃ | CH | |
| 557 | " | " | H | OCH₃ | OCH₃ | N | |
| 558 | " | " | H | OCH₃ | CH₃ | N | |
| 559 | " | " | H | OC₂H₅ | NHCH₃ | N | |
| 560 | " | " | CH₃ | OCH₃ | OCH₃ | CH | |
| 561 | " | 6-C₂H₅ | H | OCH₃ | OCH₃ | CH | |
| 562 | " | 6-C₄H₉ | H | OCH₃ | OCH₃ | CH | |
| 563 | " | 6-OC₂H₅ | H | OCH₃ | OCH₃ | CH | |
| 564 | " | 6-OCH₂CF₃ | H | OCH₃ | OCH₃ | CH | |
| 565 | " | 6-SCH₃ | H | OCH₃ | OCH₃ | CH | |
| 566 | " | 6-SO₂CH₃ | H | OCH₃ | OCH₃ | CH | |
| 567 | " | 6-NO₂ | H | OCH₃ | OCH₃ | CH | |
| 568 | " | 6-CO₂CH₃ | H | OCH₃ | OCH₃ | CH | |
| 569 | " | 6-Br | H | OCH₃ | OCH₃ | CH | |
| 570 | " | 6-CF₃ | H | OCH₃ | OCH₃ | CH | |
| 571 | " | 6-OCF₃ | H | OCH₃ | OCH₃ | CH | |
| 572 | " | 6-OCF₂H | H | OCH₃ | OCH₃ | CH | |
| 573 | —N(Et)SO₂CH₃ | H | H | OCH₃ | OCH₃ | CH | 188 (D.) |
| 574 | " | H | H | OCH₃ | CH₃ | CH | |
| 575 | " | H | H | OCH₃ | Cl | CH | |
| 576 | " | H | H | CH₃ | CH₃ | CH | |
| 577 | " | H | H | OCH₃ | OCH₃ | N | |
| 578 | " | H | H | OCH₃ | CH₃ | N | |
| 579 | " | H | H | OC₂H₅ | NHCH₃ | N | |
| 580 | " | H | CH₃ | OCH₃ | OCH₃ | CH | |
| 581 | " | 4-CH₃ | H | OCH₃ | OCH₃ | CH | |
| 582 | " | 4-Cl | H | OCH₃ | OCH₃ | CH | |
| 583 | " | 6-CH₃ | H | OCH₃ | OCH₃ | CH | |
| 584 | " | 6-OCH₃ | H | OCH₃ | OCH₃ | CH | |
| 585 | " | 6-Cl | H | OCH₃ | OCH₃ | CH | |
| 586 | " | 6-F | H | OCH₃ | OCH₃ | CH | |
| 587 | —N(Pr)SO₂H₃ | H | H | OCH₃ | OCH₃ | CH | 182–183 (D.) |
| 588 | " | H | H | OCH₃ | CH₃ | CH | |
| 589 | " | H | H | OCH₃ | Cl | CH | |
| 590 | " | H | H | CH₃ | CH₃ | CH | |
| 591 | " | H | H | OCH₃ | OCH₃ | N | |
| 592 | " | H | H | OCH₃ | CH₃ | N | |
| 593 | " | H | H | OC₂H₅ | NHCH₃ | N | |
| 594 | " | H | CH₃ | OCH₃ | OCH₃ | CH | |
| 595 | " | 4-CH₃ | H | OCH₃ | OCH₃ | CH | |
| 596 | " | 4-Cl | H | OCH₃ | OCH₃ | CH | |
| 597 | " | 6-CH₃ | H | OCH₃ | OCH₃ | CH | |
| 598 | " | 6-OCH₃ | H | OCH₃ | OCH₃ | CH | |
| 599 | " | 6-Cl | H | OCH₃ | OCH₃ | CH | |
| 600 | " | 6-F | H | OCH₃ | OCH₃ | CH | |
| 601 | —N(i-Pr)SO₂CH₃ | H | H | OCH₃ | OCH₃ | CH | 195 (D.) |
| 602 | " | H | H | OCH₃ | CH₃ | CH | |
| 603 | " | H | H | OCH₃ | Cl | CH | |
| 604 | " | H | H | CH₃ | CH₃ | CH | |
| 605 | " | H | H | OCH₃ | OCH₃ | N | |
| 606 | " | H | H | OCH₃ | CH₃ | N | |

TABLE 1-continued

| Cpd. No. | R¹ | R² | R³ | X | Y | Z | M.p. [°C.] |
|---|---|---|---|---|---|---|---|
| 607 | " | H | H | OC$_2$H$_5$ | NHCH$_3$ | N | |
| 608 | " | H | CH$_3$ | OCH$_3$ | OCH$_3$ | CH | |
| 609 | " | 4-CH$_3$ | H | OCH$_3$ | OCH$_3$ | CH | |
| 610 | " | 4-Cl | H | OCH$_3$ | OCH$_3$ | CH | |
| 611 | " | 6-CH$_3$ | H | OCH$_3$ | OCH$_3$ | CH | |
| 612 | " | 6-OCH$_3$ | H | OCH$_3$ | OCH$_3$ | CH | |
| 613 | " | 6-Cl | H | OCH$_3$ | OCH$_3$ | CH | |
| 614 | " | 6-F | H | OCH$_3$ | OCH$_3$ | CH | |
| 615 | —N(i-Bu)SO$_2$CH$_3$ | H | H | OCH$_3$ | OCH$_3$ | CH | 166–167 |
| 616 | " | H | H | OCH$_3$ | CH$_3$ | CH | |
| 617 | " | H | H | OCH$_3$ | Cl | CH | |
| 618 | " | H | H | CH$_3$ | CH$_3$ | CH | |
| 619 | " | H | H | OCH$_3$ | OCH$_3$ | N | |
| 620 | " | H | H | OCH$_3$ | CH$_3$ | N | |
| 621 | " | H | H | OC$_2$H$_5$ | NHCH$_3$ | N | |
| 622 | " | H | CH$_3$ | OCH$_3$ | OCH$_3$ | CH | |
| 623 | " | 4-CH$_3$ | H | OCH$_3$ | OCH$_3$ | CH | |
| 624 | " | 4-Cl | H | OCH$_3$ | OCH$_3$ | CH | |
| 625 | " | 6-CH$_3$ | H | OCH$_3$ | OCH$_3$ | CH | |
| 626 | " | 6-OCH$_3$ | H | OCH$_3$ | OCH$_3$ | CH | |
| 627 | " | 6-Cl | H | OCH$_3$ | OCH$_3$ | CH | |
| 628 | " | 6-F | H | OCH$_3$ | OCH$_3$ | CH | |
| 629 | —N(CF$_3$)SO$_2$CH$_3$ | H | H | OCH$_3$ | OCH$_3$ | CH | |
| 630 | " | H | H | OCH$_3$ | CH$_3$ | CH | |
| 631 | " | H | H | OCH$_3$ | Cl | CH | |
| 632 | " | H | H | CH$_3$ | CH$_3$ | CH | |
| 633 | " | H | H | OCH$_3$ | OCH$_3$ | N | |
| 634 | " | H | H | OCH$_3$ | CH$_3$ | N | |
| 635 | " | H | H | OC$_2$H$_5$ | NHCH$_3$ | N | |
| 636 | " | H | CH$_3$ | OCH$_3$ | OCH$_3$ | CH | |
| 637 | " | 4-CH$_3$ | H | OCH$_3$ | OCH$_3$ | CH | |
| 638 | " | 4-Cl | H | OCH$_3$ | OCH$_3$ | CH | |
| 639 | " | 6-CH$_3$ | H | OCH$_3$ | OCH$_3$ | CH | |
| 640 | " | 6-OCH$_3$ | H | OCH$_3$ | OCH$_3$ | CH | |
| 641 | " | 6-Cl | H | OCH$_3$ | OCH$_3$ | CH | |
| 642 | " | 6-F | H | OCH$_3$ | OCH$_3$ | CH | |
| 643 | —N(CHF$_2$)SO$_2$CH$_3$ | H | H | OCH$_3$ | OCH$_3$ | CH | |
| 644 | " | H | H | OCH$_3$ | CH$_3$ | CH | |
| 645 | " | H | H | OCH$_3$ | Cl | CH | |
| 646 | " | H | H | CH$_3$ | CH$_3$ | CH | |
| 647 | " | H | H | OCH$_3$ | OCH$_3$ | N | |
| 648 | " | H | H | OCH$_3$ | CH$_3$ | N | |
| 649 | " | H | H | OC$_2$H$_5$ | NHCH$_3$ | N | |
| 650 | " | H | CH$_3$ | OCH$_3$ | OCH$_3$ | CH | |
| 651 | " | 4-CH$_3$ | H | OCH$_3$ | OCH$_3$ | CH | |
| 652 | " | 4-Cl | H | OCH$_3$ | OCH$_3$ | CH | |
| 653 | " | 6-CH$_3$ | H | OCH$_3$ | OCH$_3$ | CH | |
| 654 | " | 6-OCH$_3$ | H | OCH$_3$ | OCH$_3$ | CH | |
| 655 | " | 6-Cl | H | OCH$_3$ | OCH$_3$ | CH | |
| 656 | " | 6-F | H | OCH$_3$ | OCH$_3$ | CH | |
| 657 | —N(CH$_2$CF$_3$)(SO$_2$CH$_3$) | H | H | OCH$_3$ | OCH$_3$ | CH | |
| 658 | " | H | H | OCH$_3$ | CH$_3$ | CH | |
| 659 | " | H | H | OCH$_3$ | Cl | CH | |
| 660 | " | H | H | CH$_3$ | CH$_3$ | CH | |
| 661 | " | H | H | OCH$_3$ | OCH$_3$ | N | |
| 662 | " | H | H | OCH$_3$ | CH$_3$ | N | |
| 663 | " | H | H | OC$_2$H$_5$ | NHCH$_3$ | N | |
| 664 | " | H | CH$_3$ | OCH$_3$ | OCH$_3$ | CH | |
| 665 | " | 4-CH$_3$ | H | OCH$_3$ | OCH$_3$ | CH | |
| 666 | " | 4-Cl | H | OCH$_3$ | OCH$_3$ | CH | |
| 667 | " | 6-CH$_3$ | H | OCH$_3$ | OCH$_3$ | CH | |
| 668 | " | 6-OCH$_3$ | H | OCH$_3$ | OCH$_3$ | CH | |

TABLE 1-continued

| Cpd. No. | R¹ | R² | R³ | X | Y | Z | M.p. [°C.] |
|---|---|---|---|---|---|---|---|
| 669 | " | 6-Cl | H | OCH₃ | OCH₃ | CH | |
| 670 | " | 6-F | H | OCH₃ | OCH₃ | CH | |
| 671 | −N(CH₂CH₂Cl)(SO₂CH₃) | H | H | OCH₃ | OCH₃ | CH | |
| 672 | " | H | H | OCH₃ | CH₃ | CH | |
| 673 | " | H | H | OCH₃ | Cl | CH | |
| 674 | " | H | H | CH₃ | CH₃ | CH | |
| 675 | " | H | H | OCH₃ | OCH₃ | N | |
| 676 | " | H | H | OCH₃ | CH₃ | N | |
| 677 | " | H | H | OC₂H₅ | NHCH₃ | N | |
| 678 | " | H | CH₃ | OCH₃ | OCH₃ | CH | |
| 679 | " | 4-CH₃ | H | OCH₃ | OCH₃ | CH | |
| 680 | " | 4-Cl | H | OCH₃ | OCH₃ | CH | |
| 681 | " | 6-CH₃ | H | OCH₃ | OCH₃ | CH | |
| 682 | " | 6-OCH₃ | H | OCH₃ | OCH₃ | CH | |
| 683 | " | 6-Cl | H | OCH₃ | OCH₃ | CH | |
| 684 | " | 6-F | H | OCH₃ | OCH₃ | CH | |
| 685 | −N(CH₂CH₂OCH₃)(SO₂CH₃) | H | H | OCH₃ | OCH₃ | CH | |
| 686 | " | H | H | OCH₃ | CH₃ | CH | |
| 687 | " | H | H | OCH₃ | Cl | CH | |
| 688 | " | H | H | CH₃ | CH₃ | CH | |
| 689 | " | H | H | OCH₃ | OCH₃ | N | |
| 690 | " | H | H | OCH₃ | CH₃ | N | |
| 691 | " | H | H | OC₂H₅ | NHCH₃ | N | |
| 692 | " | H | CH₃ | OCH₃ | OCH₃ | CH | |
| 693 | " | 4-CH₃ | H | OCH₃ | OCH₃ | CH | |
| 694 | " | 4-Cl | H | OCH₃ | OCH₃ | CH | |
| 695 | " | 6-CH₃ | H | OCH₃ | OCH₃ | CH | |
| 696 | " | 6-OCH₃ | H | OCH₃ | OCH₃ | CH | |
| 697 | " | 6-Cl | H | OCH₃ | OCH₃ | CH | |
| 698 | " | 6-F | H | OCH₃ | OCH₃ | CH | |
| 699 | −N(CH₂SCH₃)(SO₂CH₃) | H | H | OCH₃ | OCH₃ | CH | |
| 700 | " | H | H | OCH₃ | CH₃ | CH | |
| 701 | " | H | H | OCH₃ | Cl | CH | |
| 702 | " | H | H | CH₃ | CH₃ | CH | |
| 703 | " | H | H | OCH₃ | OCH₃ | N | |
| 704 | " | H | H | OCH₃ | CH₃ | N | |
| 706 | " | H | H | OC₂H₅ | NHCH₃ | N | |
| 707 | " | H | CH₃ | OCH₃ | OCH₃ | CH | |
| 708 | " | 4-CH₃ | H | OCH₃ | OCH₃ | CH | |
| 709 | " | 4-Cl | H | OCH₃ | OCH₃ | CH | |
| 710 | " | 6-CH₃ | H | OCH₃ | OCH₃ | CH | |
| 711 | " | 6-OCH₃ | H | OCH₃ | OCH₃ | CH | |
| 712 | " | 6-Cl | H | OCH₃ | OCH₃ | CH | |
| 713 | " | 6-F | H | OCH₃ | OCH₃ | CH | |
| 714 | −N(CH₂SO₂CH₃)(SO₂CH₃) | H | H | OCH₃ | OCH₃ | CH | |

TABLE 1-continued

| Cpd. No. | R¹ | R² | R³ | X | Y | Z | M.p. [°C.] |
|---|---|---|---|---|---|---|---|
| 715 | " | H | H | OCH₃ | CH₃ | CH | |
| 716 | " | H | H | OCH₃ | Cl | CH | |
| 717 | " | H | H | CH₃ | CH₃ | CH | |
| 718 | " | H | H | OCH₃ | OCH₃ | N | |
| 719 | " | H | H | OCH₃ | CH₃ | N | |
| 720 | " | H | H | OC₂H₅ | NHCH₃ | N | |
| 721 | " | H | CH₃ | OCH₃ | OCH₃ | CH | |
| 722 | " | 4-CH₃ | H | OCH₃ | OCH₃ | CH | |
| 723 | " | 4-Cl | H | OCH₃ | OCH₃ | CH | |
| 724 | " | 6-CH₃ | H | OCH₃ | OCH₃ | CH | |
| 725 | " | 6-OCH₃ | H | OCH₃ | OCH₃ | CH | |
| 726 | " | 6-Cl | H | OCH₃ | OCH₃ | CH | |
| 727 | " | 6-F | H | OCH₃ | OCH₃ | CH | |
| 728 | —N(CH₂CO₂CH₃)(SO₂CH₃) | H | H | OCH₃ | OCH₃ | CH | |
| 729 | " | H | H | OCH₃ | CH₃ | CH | |
| 730 | " | H | H | OCH₃ | Cl | CH | |
| 731 | " | H | H | CH₃ | CH₃ | CH | |
| 732 | " | H | H | OCH₃ | OCH₃ | N | |
| 733 | " | H | H | OCH₃ | CH₃ | N | |
| 734 | " | H | H | OC₂H₅ | NHCH₃ | N | |
| 735 | " | H | CH₃ | OCH₃ | OCH₃ | CH | |
| 736 | " | 4-CH₃ | H | OCH₃ | OCH₃ | CH | |
| 737 | " | 4-Cl | H | OCH₃ | OCH₃ | CH | |
| 738 | " | 6-CH₃ | H | OCH₃ | OCH₃ | CH | |
| 739 | " | 6-OCH₃ | H | OCH₃ | OCH₃ | CH | |
| 740 | " | 6-Cl | H | OCH₃ | OCH₃ | CH | |
| 741 | " | 6-F | H | OCH₃ | OCH₃ | CH | |
| 742 | —N(CH₂CN)(SO₂CH₃) | H | H | OCH₃ | OCH₃ | CH | |
| 743 | " | H | H | OCH₃ | CH₃ | CH | |
| 744 | " | H | H | OCH₃ | Cl | CH | |
| 745 | " | H | H | CH₃ | CH₃ | CH | |
| 746 | " | H | H | OCH₃ | OCH₃ | N | |
| 747 | " | H | H | OCH₃ | CH₃ | N | |
| 748 | " | H | H | OC₂H₅ | NHCH₃ | N | |
| 749 | " | H | CH₃ | OCH₃ | OCH₃ | CH | |
| 750 | " | 4-CH₃ | H | OCH₃ | OCH₃ | CH | |
| 751 | " | 4-Cl | H | OCH₃ | OCH₃ | CH | |
| 752 | " | 6-CH₃ | H | OCH₃ | OCH₃ | CH | |
| 753 | " | 6-OCH₃ | H | OCH₃ | OCH₃ | CH | |
| 754 | " | 6-Cl | H | OCH₃ | OCH₃ | CH | |
| 755 | " | 6-F | H | OCH₃ | OCH₃ | CH | |
| 756 | —N(Allyl)(SO₂CH₃) | H | H | OCH₃ | OCH₃ | CH | 208–210 (D.) |
| 757 | " | H | H | OCH₃ | CH₃ | CH | |
| 758 | " | H | H | OCH₃ | Cl | CH | |
| 759 | " | H | H | CH₃ | CH₃ | CH | |
| 760 | " | H | H | OCH₃ | OCH₃ | N | |
| 761 | " | H | H | OCH₃ | CH₃ | N | |
| 762 | " | H | H | OC₂H₅ | NHCH₃ | N | |
| 763 | " | H | CH₃ | OCH₃ | OCH₃ | CH | |
| 764 | " | 4-CH₃ | H | OCH₃ | OCH₃ | CH | |
| 765 | " | 4-Cl | H | OCH₃ | OCH₃ | CH | |

TABLE 1-continued

| Cpd. No. | R¹ | R² | R³ | X | Y | Z | M.p. [°C.] |
|---|---|---|---|---|---|---|---|
| 766 | " | 6-CH₃ | H | OCH₃ | OCH₃ | CH | |
| 767 | " | 6-OCH₃ | H | OCH₃ | OCH₃ | CH | |
| 768 | " | 6-Cl | H | OCH₃ | OCH₃ | CH | |
| 769 | " | 6-F | H | OCH₃ | OCH₃ | CH | |
| 770 | —N(Propargyl)(SO₂CH₃) | H | H | OCH₃ | OCH₃ | CH | 167–168 (D.) |
| 771 | " | H | H | OCH₃ | CH₃ | CH | |
| 772 | " | H | H | OCH₃ | Cl | CH | |
| 773 | " | H | H | CH₃ | CH₃ | CH | |
| 774 | " | H | H | OCH₃ | OCH₃ | N | |
| 775 | " | H | H | OCH₃ | CH₃ | N | |
| 776 | " | H | H | OC₂H₅ | NHCH₃ | N | |
| 777 | " | H | CH₃ | OCH₃ | OCH₃ | CH | |
| 778 | " | 4-CH₃ | H | OCH₃ | OCH₃ | CH | |
| 779 | " | 4-Cl | H | OCH₃ | OCH₃ | CH | |
| 780 | " | 6-CH₃ | H | OCH₃ | OCH₃ | CH | |
| 781 | " | 6-OCH₃ | H | OCH₃ | OCH₃ | CH | |
| 782 | " | 6-Cl | H | OCH₃ | OCH₃ | CH | |
| 783 | " | 6-F | H | OCH₃ | OCH₃ | CH | |
| 784 | —N(COCH₃)(SO₂CH₃) | H | H | OCH₃ | OCH₃ | CH | |
| 785 | " | H | H | OCH₃ | CH₃ | CH | |
| 786 | " | H | H | OCH₃ | Cl | CH | |
| 787 | " | H | H | CH₃ | CH₃ | CH | |
| 788 | " | H | H | OCH₃ | OCH₃ | N | |
| 789 | " | H | H | OCH₃ | CH₃ | N | |
| 790 | " | H | H | OC₂H₅ | NHCH₃ | N | |
| 791 | " | H | CH₃ | OCH₃ | OCH₃ | CH | |
| 792 | " | 4-CH₃ | H | OCH₃ | OCH₃ | CH | |
| 793 | " | 4-Cl | H | OCH₃ | OCH₃ | CH | |
| 794 | " | 6-CH₃ | H | OCH₃ | OCH₃ | CH | |
| 795 | " | 6-OCH₃ | H | OCH₃ | OCH₃ | CH | |
| 796 | " | 6-Cl | H | OCH₃ | OCH₃ | CH | |
| 797 | " | 6-F | H | OCH₃ | OCH₃ | CH | |
| 798 | (isothiazolidine-1,1-dioxide) | H | H | OCH₃ | OCH₃ | CH | 195 (D.) |
| 799 | " | H | H | OCH₃ | CH₃ | CH | |
| 800 | " | H | H | OCH₃ | Cl | CH | |
| 801 | " | H | H | CH₃ | CH₃ | CH | |
| 802 | " | H | H | OCH₃ | OCH₃ | N | |
| 803 | " | H | H | OCH₃ | CH₃ | N | |
| 804 | " | H | H | OC₂H₅ | NHCH₃ | N | |
| 805 | " | H | CH₃ | OCH₃ | OCH₃ | CH | |
| 806 | " | 4-CH₃ | H | OCH₃ | OCH₃ | CH | |
| 807 | " | 4-Cl | H | OCH₃ | OCH₃ | CH | |
| 808 | " | 6-CH₃ | H | OCH₃ | OCH₃ | CH | |
| 809 | " | 6-OCH₃ | H | OCH₃ | OCH₃ | CH | |
| 810 | " | 6-Cl | H | OCH₃ | OCH₃ | CH | |
| 811 | " | 6-F | H | OCH₃ | OCH₃ | CH | |

TABLE 1-continued

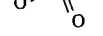

| Cpd. No. | R¹ | R² | R³ | X | Y | Z | M.p. [°C.] |
|---|---|---|---|---|---|---|---|
| 812 | (see structure below) | H | H | OCH₃ | OCH₃ | CH | 192–193 (D.) |
| 813 | " | H | H | OCH₃ | CH₃ | CH | |
| 814 | " | H | H | OCH₃ | Cl | CH | |
| 815 | " | H | H | CH₃ | CH₃ | CH | |
| 816 | " | H | H | OCH₃ | OCH₃ | N | |
| 817 | " | H | H | OCH₃ | CH₃ | N | |
| 818 | " | H | H | OC₂H₅ | NHCH₃ | N | |
| 819 | " | H | CH₃ | OCH₃ | OCH₃ | CH | |
| 820 | " | 4-CH₃ | H | OCH₃ | OCH₃ | CH | |
| 821 | " | 4-Cl | H | OCH₃ | OCH₃ | CH | |
| 822 | " | 6-CH₃ | H | OCH₃ | OCH₃ | CH | |
| 823 | " | 6-OCH₃ | H | OCH₃ | OCH₃ | CH | |
| 824 | " | 6-Cl | H | OCH₃ | OCH₃ | CH | |
| 825 | " | 6-F | H | OCH₃ | OCH₃ | CH | |
| 826 | —N(OCH₃)SO₂CH₃ | H | H | OCH₃ | OCH₃ | CH | |
| 827 | " | H | H | OCH₃ | CH₃ | CH | |
| 828 | " | H | H | OCH₃ | Cl | CH | |
| 829 | " | H | H | CH₃ | CH₃ | CH | |
| 830 | " | H | H | OCH₃ | OCH₃ | N | |
| 831 | " | H | H | OCH₃ | CH₃ | N | |
| 832 | " | H | H | OC₂H₅ | NHCH₃ | N | |
| 833 | " | H | CH₃ | OCH₃ | OCH₃ | CH | |
| 834 | " | 4-CH₃ | H | OCH₃ | OCH₃ | CH | |
| 835 | " | 4-Cl | H | OCH₃ | OCH₃ | CH | |
| 836 | " | 6-CH₃ | H | OCH₃ | OCH₃ | CH | |
| 837 | " | 6-OCH₃ | H | OCH₃ | OCH₃ | CH | |
| 838 | " | 6-Cl | H | OCH₃ | OCH₃ | CH | |
| 839 | " | 6-F | H | OCH₃ | OCH₃ | CH | |
| 840 | —N(CH₃)SO₂CH₃ | H | H | OCH₃ | OCH₃ | CH | |
| 841 | " | H | H | OCH₃ | CH₃ | CH | |
| 842 | " | H | H | OCH₃ | Cl | CH | |
| 843 | " | H | H | CH₃ | CH₃ | CH | |
| 844 | " | H | H | OCH₃ | OCH₃ | N | |
| 845 | " | H | H | OCH₃ | CH₃ | N | |
| 846 | " | H | H | OC₂H₅ | NHCH₃ | N | |
| 847 | " | H | CH₃ | OCH₃ | OCH₃ | CH | |
| 848 | " | 4-CH₃ | H | OCH₃ | OCH₃ | CH | |
| 849 | " | 4-Cl | H | OCH₃ | OCH₃ | CH | |
| 850 | " | 6-CH₃ | H | OCH₃ | OCH₃ | CH | |
| 851 | " | 6-OCH₃ | H | OCH₃ | OCH₃ | CH | |
| 852 | " | 6-Cl | H | OCH₃ | OCH₃ | CH | |
| 853 | " | 6-F | H | OCH₃ | OCH₃ | CH | |
| 854 | —N(CH₃)SO₂Et | H | H | OCH₃ | OCH₃ | CH | 176–177 |
| 855 | " | H | H | OCH₃ | CH₃ | CH | |
| 856 | " | H | H | OCH₃ | Cl | CH | |
| 857 | " | H | H | CH₃ | CH₃ | CH | |
| 858 | " | H | H | OCH₃ | OCH₃ | N | |
| 859 | " | H | H | OCH₃ | CH₃ | N | |
| 860 | " | H | H | OC₂H₅ | NHCH₃ | N | |
| 861 | " | H | CH₃ | OCH₃ | OCH₃ | CH | |
| 862 | " | 4-CH₃ | H | OCH₃ | OCH₃ | CH | |
| 863 | " | 4-Cl | H | OCH₃ | OCH₃ | CH | |
| 864 | " | 6-CH₃ | H | OCH₃ | OCH₃ | CH | 193–194 (D.) |
| 865 | " | 6-OCH₃ | H | OCH₃ | OCH₃ | CH | |
| 866 | " | 6-Cl | H | OCH₃ | OCH₃ | CH | |
| 867 | " | 6-F | H | OCH₃ | OCH₃ | CH | |
| 868 | —N(CH₃)SO₂Ph | H | H | OCH₃ | OCH₃ | CH | |
| 869 | " | H | H | OCH₃ | CH₃ | CH | |
| 870 | " | H | H | OCH₃ | Cl | CH | |
| 871 | " | H | H | CH₃ | CH₃ | CH | |
| 872 | " | H | H | OCH₃ | OCH₃ | N | |

R¹ for 812 (and following marked "):

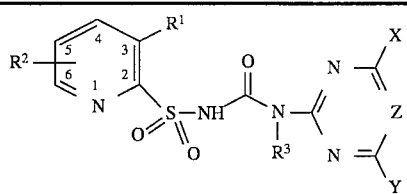

TABLE 1-continued

| Cpd. No. | R¹ | R² | R³ | X | Y | Z | M.p. [°C.] |
|---|---|---|---|---|---|---|---|
| 873 | " | H | H | OCH₃ | CH₃ | N | |
| 874 | " | H | H | OC₂H₅ | NHCH₃ | N | |
| 875 | " | H | CH₃ | OCH₃ | OCH₃ | CH | |
| 876 | " | 4-CH₃ | H | OCH₃ | OCH₃ | CH | |
| 877 | " | 4-Cl | H | OCH₃ | OCH₃ | CH | |
| 878 | " | 6-CH₃ | H | OCH₃ | OCH₃ | CH | |
| 879 | " | 6-OCH₃ | H | OCH₃ | OCH₃ | CH | |
| 880 | " | 6-Cl | H | OCH₃ | OCH₃ | CH | |
| 881 | " | 6-F | H | OCH₃ | OCH₃ | CH | |
| 882 | —N(CH₃)SO₂NMe₂ | H | H | OCH₃ | OCH₃ | CH | |
| 883 | " | H | H | OCH₃ | CH₃ | CH | |
| 884 | " | H | H | OCH₃ | Cl | CH | |
| 885 | " | H | H | OCH₃ | CH₃ | CH | |
| 886 | " | H | H | OCH₃ | OCH₃ | N | |
| 887 | " | H | H | OCH₃ | CH₃ | N | |
| 888 | " | H | H | OC₂H₅ | NHCH₃ | N | |
| 889 | " | H | H | OCH₃ | OCH₃ | CH | |
| 890 | " | 4-CH₃ | H | OCH₃ | OCH₃ | CH | |
| 891 | " | 4-Cl | H | OCH₃ | OCH₃ | CH | |
| 892 | " | 6-CH₃ | H | OCH₃ | OCH₃ | CH | |
| 893 | " | 6-OCH₃ | H | OCH₃ | OCH₃ | CH | |
| 894 | " | 6-Cl | H | OCH₃ | OCH₃ | CH | |
| 895 | " | 6-F | H | OCH₃ | OCH₃ | CH | |

TABLE 2

| Cpd. No. | R¹ | R² | R³ | X | Y | Z | M.p. [°C.] |
|---|---|---|---|---|---|---|---|
| 896 | I | H | H | OCH₃ | OCH₃ | CH | |
| 897 | " | H | H | OCH₃ | CH₃ | CH | |
| 898 | " | H | H | OCH₃ | Cl | CH | |
| 899 | " | H | H | CH₃ | CH₃ | CH | |
| 900 | " | H | H | OCH₃ | OCH₃ | N | |
| 901 | " | H | H | OCH₃ | CH₃ | N | |
| 902 | " | H | H | OC₂H₅ | NHCH₃ | N | |
| 903 | " | H | CH₃ | OCH₃ | OCH₃ | CH | |
| 904 | " | 4-CH₃ | H | OCH₃ | OCH₃ | CH | |
| 905 | " | 6-CH₃ | H | OCH₃ | OCH₃ | CH | |
| 906 | " | 4-Cl | H | OCH₃ | OCH₃ | CH | |
| 907 | " | 6-Cl | H | OCH₃ | OCH₃ | CH | |
| 908 | " | 4-F | H | OCH₃ | OCH₃ | CH | |
| 909 | " | 6-F | H | OCH₃ | OCH₃ | CH | |
| 910 | " | 4-OCH₃ | H | OCH₃ | OCH₃ | CH | |
| 911 | " | 6-OCH₃ | H | OCH₃ | OCH₃ | CH | |
| 912 | —OSO₂N(CH₃)₂ | H | H | OCH₃ | OCH₃ | CH | |
| 913 | " | 4-CH₃ | H | OCH₃ | OCH₃ | CH | |
| 914 | " | 6-CH₃ | H | OCH₃ | OCH₃ | CH | |
| 915 | " | 4-Cl | H | OCH₃ | OCH₃ | CH | |
| 916 | " | 6-Cl | H | OCH₃ | OCH₃ | CH | |
| 917 | " | 4-F | H | OCH₃ | OCH₃ | CH | |
| 918 | " | 6-F | H | OCH₃ | OCH₃ | CH | |
| 919 | " | 4-OCH₃ | H | OCH₃ | OCH₃ | CH | |
| 920 | " | 6-OCH₃ | H | OCH₃ | OCH₃ | CH | |
| 921 | —N(CH₃)SO₂CH₃ | H | H | OCH₃ | OCH₃ | CH | |
| 922 | " | H | H | OCH₃ | CH₃ | CH | |
| 923 | " | H | H | OCH₃ | Cl | CH | |
| 924 | " | H | H | CH₃ | CH₃ | CH | |

TABLE 2-continued

| Cpd. No. | R¹ | R² | R³ | X | Y | Z | M.p. [°C.] |
|---|---|---|---|---|---|---|---|
| 925 | " | H | H | OCH₃ | OCH₃ | N | |
| 926 | " | H | H | OCH₃ | CH₃ | N | |
| 927 | " | H | H | OC₂H₅ | NHCH₃ | N | |
| 928 | " | H | CH₃ | OCH₃ | OCH₃ | CH | |
| 929 | " | 4-CH₃ | H | OCH₃ | OCH₃ | CH | |
| 930 | " | 6-CH₃ | H | OCH₃ | OCH₃ | CH | |
| 931 | " | 4-Cl | H | OCH₃ | OCH₃ | CH | |
| 932 | " | 6-Cl | H | OCH₃ | OCH₃ | CH | |
| 933 | " | 4-F | H | OCH₃ | OCH₃ | CH | |
| 934 | " | 6-F | H | OCH₃ | OCH₃ | CH | |
| 935 | " | 4-OCH₃ | H | OCH₃ | OCH₃ | CH | |
| 936 | " | 6-OCH₃ | H | OCH₃ | OCH₃ | CH | |
| 937 | —NHSO₂CH₃ | H | H | OCH₃ | OCH₃ | CH | |
| 938 | —NHSO₂C₂H₅ | H | H | OCH₃ | OCH₃ | CH | |
| 939 | —N(SO₂CH₃)₂ | H | H | OCH₃ | OCH₃ | CH | |
| 940 | —N(CH₃)SO₂Et | H | H | OCH₃ | OCH₃ | CH | |
| 941 | —N(Et)SO₂CH₃ | H | H | OCH₃ | OCH₃ | CH | |

TABLE 3

| Cpd. No. | R¹ | A |
|---|---|---|
| 942 | I | 4-OCH₃, 2-unsubst., fused dihydrofuran pyrimidine |
| 943 | —OSO₂N(CH₂)₂ | 4-CH₃, fused dihydrofuran pyrimidine |
| 944 | I | 4-CH₃, fused (O, CH₃) furan pyrimidine |
| 945 | —OSO₂N(CH₃)₂ | 4-OCH₃, fused (O, CH₃) furan pyrimidine |
| 946 | I | 4-CH₃, fused (O, OCH₃) furan pyrimidine |
| 947 | —OSO₂N(CH₃)₂ | N-methyl-triazole-OCH₃ |
| 948 | I | N-methyl-triazole-SCH₃ |
| 949 | —OSO₂N(CH₃)₂ | —CH₂— bis(OCH₃)-triazine |

TABLE 3-continued

[Structure: pyridine with R¹ substituent, -SO₂-NH-C(O)-NH-A]

| Cpd. No. | R¹ | A |
|---|---|---|
| 950 | I | 3-CN, 4-OCH₃, 6-CH₃-pyridin-2-yl |
| 951 | —OSO₂N(CH₃)₂ | 3-CN, 4-CH₃, 6-OCH₃-pyridin-2-yl |
| 952 | I | 3-CN, 4-OCH₃, 6-OCH₃-pyridin-2-yl |
| 953 | —OSO₂N(CH₃)₂ | 4-CH₃, 6-OCH₃-pyrimidin-2-yl |
| 954 | I | 4-CH₃, 6-Cl-pyrimidin-2-yl |
| 955 | —N(CH₃)SO₂CH₃ | 4-OCH₃, furo-pyrimidinyl |
| 956 | " | 4-CH₃, furo-pyrimidinyl |
| 957 | " | 4-CH₃, 6-CH₃-pyrano-pyrimidinyl |
| 958 | " | 4-OCH₃, 6-CH₃-pyrano-pyrimidinyl |
| 959 | " | 4-CH₃, 6-OCH₃-pyrano-pyrimidinyl |
| 960 | —N(CH₃)SO₂CH₃ | N-methyl-triazinyl-OCH₃ |
| 961 | " | N-methyl-triazinyl-SCH₃ |
| 962 | " | —CH₂-triazinyl(OCH₃)₂ |
| 963 | " | 3-CN, 4-OCH₃, 6-CH₃-pyridin-2-yl |
| 964 | " | 3-CN, 4-CH₃, 6-OCH₃-pyridin-2-yl |

TABLE 3-continued

Structure: pyridine with R¹ at position 3, -S(=O)(=O)-NH-C(=O)-NH-A substituent at position 2

| Cpd. No. | R¹ | A |
|---|---|---|
| 965 | " | pyridine with CN, OCH₃, CH₃, OCH₃ substituents |
| 966 | " | triazine with CH₃ and OCH₃ |
| 967 | " | triazine with CH₃ and Cl |

TABLE 4

Structure: pyridine with R¹ at position 3, R² at positions 4/5/6, -S(=O)(=O)-NH₂ at position 2

| Cpd. No. | R¹ | R² | M.p. [°C.] |
|---|---|---|---|
| 968 | I | H | 247–250 (dec.) |
| 969 | " | 4-CH₃ | |
| 970 | " | 5-CH₃ | |
| 971 | " | 6-CH₃ | |
| 972 | " | 4-OCH₃ | |
| 973 | " | 5-OCH₃ | |
| 974 | " | 6-OCH₃ | |
| 975 | " | 4-Cl | |
| 976 | " | 5-Cl | |
| 977 | " | 6-Cl | |
| 978 | " | 4-F | |
| 979 | " | 5-F | |
| 980 | " | 6-F | |
| 981 | " | 6-C₂H₅ | |
| 982 | " | 6-C₄H₉ | |
| 983 | " | 6-OC₂H₅ | |
| 984 | " | 6-OCH₂CF₃ | |
| 985 | " | 6-SCH₃ | |
| 986 | " | 6-SO₂CH₃ | |
| 987 | " | 6-NO₂ | |
| 988 | " | 6-CO₂CH₃ | |
| 989 | " | 6-Br | |
| 990 | " | 6-CF₃ | |
| 991 | " | 6-OCF₃ | |
| 992 | " | 6-OCF₂H | |
| 993 | —OSO₂N(CH₃)₂ | H | oil |
| 994 | " | 4-CH₃ | |
| 995 | " | 5-CH₃ | |
| 996 | " | 6-CH₃ | |
| 997 | " | 4-OCH₃ | |
| 998 | " | 5-OCH₃ | |
| 999 | " | 6-OCH₃ | |
| 1000 | " | 4-Cl | |
| 1001 | " | 5-Cl | |
| 1002 | " | 6-Cl | |
| 1003 | " | 4-F | |
| 1004 | " | 5-F | |
| 1005 | " | 6-F | |
| 1006 | " | 6-C₂H₅ | |
| 1007 | " | 6-C₄H₉ | |
| 1008 | " | 6-OC₂H₅ | |
| 1009 | " | 6-OCH₂CF₃ | |
| 1010 | " | 6-SCH₃ | |
| 1011 | " | 6-SO₂CH₃ | |
| 1012 | " | 6-NO₂ | |
| 1013 | " | 6-CO₂CH₃ | |
| 1014 | " | 6-Br | |
| 1015 | " | 6-CF₃ | |
| 1016 | " | 6-OCF₃ | |
| 1017 | " | 6-OCF₂H | |
| 1018 | —OSO₂—N(CH₃)(C₂H₅) | H | |
| 1019 | —OSO₂—N(CH₃)(C₃H₇) | H | |
| 1020 | —OSO₂—N(C₂H₅)₂ | H | 94–97 |
| 1021 | —OSO₂—N(pyrrolidinyl) | H | 142–143 |
| 1022 | —OSO₂—N(piperidinyl) | H | 166–167 |
| 1023 | —OSO₂—N(morpholinyl) | H | oil |
| 1024 | —NHSO₂CH₃ | H | 176–178 |
| 1025 | —NHSO₂C₂H₅ | H | |
| 1026 | —NHSO₂C₃H₇ | H | |
| 1027 | —NHSO₂C₆H₅ | H | |
| 1028 | —N(SO₂CH₃)₂ | H | 208 |
| 1029 | —N(SO₂C₂H₅)₂ | H | |
| 1030 | —N(CH₃)SO₂CH₃ | H | 175 |
| 1031 | " | 4-CH₃ | |
| 1032 | " | 5-CH₃ | |
| 1033 | " | 6-CH₃ | 124 |
| 1034 | " | 4-OCH₃ | |
| 1035 | " | 5-OCH₃ | |
| 1036 | " | 6-OCH₃ | |
| 1037 | " | 4-Cl | |
| 1038 | " | 5-Cl | |
| 1039 | " | 6-Cl | |

TABLE 4-continued

R²—[pyridine ring with R¹ at position 3]—S(=O)(=O)—NH₂

| Cpd. No. | R¹ | R² | M.p. [°C.] |
|---|---|---|---|
| 1040 | " | 4-F | |
| 1041 | " | 5-F | |
| 1042 | " | 6-F | |
| 1043 | " | 6-C₂H₅ | |
| 1044 | " | 6-C₄H₉ | |
| 1045 | " | 6-OC₂H₅ | |
| 1046 | " | 6-OCH₂CF₃ | |
| 1047 | " | 6-SCH₃ | |
| 1048 | " | 6-SO₂CH₃ | |
| 1049 | " | 6-NO₂ | |
| 1050 | " | 6-CO₂CH₃ | |
| 1051 | " | 6-Br | |
| 1052 | " | 6-CF₃ | |
| 1053 | " | 6-OCF₃ | |
| 1054 | " | 6-OCF₂H | |
| 1055 | —N(Et)SO₂CH₃ | H | 178–179 (D.) |
| 1056 | —N(Pr)SO₂CH₃ | H | 149–150 |
| 1057 | —N(i-Pr)SO₂CH₃ | H | 201 |
| 1058 | —N(i-Bu)SO₂CH₃ | H | amorphous |
| 1059 | —N(CH₂CF₃)(SO₂CH₃) | H | |
| 1060 | —N(CH₂CH₂Cl)(SO₂CH₃) | H | |
| 1061 | —N(CH₂CH₂OCH₃)(SO₂CH₃) | H | |
| 1062 | —N(CH₂SCH₃)(SO₂CH₃) | H | |
| 1063 | —N(CH₂SO₂CH₃)(SO₂CH₃) | H | |
| 1064 | —N(CH₂CO₂CH₃)(SO₂CH₃) | H | |
| 1065 | —N(CH₂CN)(SO₂CH₃) | H | |
| 1066 | —N(Allyl)(SO₂CH₃) | H | 143–144 |
| 1067 | —N(Propargyl)(SO₂CH₃) | H | 138–141 |
| 1068 | —N(COCH₃)(SO₂CH₃) | H | |
| 1069 | —N(cyclic-SO₂, 5-ring) | H | 200 (D.) |
| 1070 | —N(cyclic-SO₂, 6-ring) | H | 220–221 (D.) |
| 1071 | —N(OCH₃)SO₂CH₃ | H | |
| 1072 | —N(CH₃)SO₂C₂H₅ | H | 136–137 |
| 1073 | —N(CH₃)SO₂CF₃ | H | |
| 1074 | —N(CH₃)SO₂Ph | H | 200–203 |
| 1075 | —N(CH₃)SO₂N(Me)₂ | H | |

B. FORMULATION EXAMPLES a) A dusting agent is obtained by mixing 10 parts by weight of a compound of the formula (I) and 90 parts by weight of talc or inert material and comminuting in a hammer mill.

b) A wettable powder which is easily dispersible in water is obtained by mixing 25 parts by weight of a compound of the formula (I), 64 parts by weight of kaolin-containing quartz as inert material, 10 parts by weight of potassium ligninsulfonate and 1 part by weight of sodium oleylmethyltaurate as wetting agent and dispersant and grinding in a pin-disk mill.

c) A dispersion concentrate which is easily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255 to over 277° C.) and grinding to a fineness of less than 5 microns in a friction ball mill.

d) An emulsifiable concentrate is obtained from 15 parts by weight of a compound of the formula (I), 75 parts by weight of cyclohexane as solvent and 10 parts by weight of ethoxylated nonylphenol as emulsifier.

e) Granules which are dispersible in water are obtained by mixing 75 parts by weight of a compound of the formula (I)
10 parts by weight of calcium ligninsulfonate,
5 parts by weight of sodium lauryl sulfate, -continued 3 parts by weight of polyvinyl alcohol and
7 parts by weight of kaolin, grinding in a pinned-disk mill and granulating the powder in a fluidized bed by spraying water as a granulating fluid.

f) Granules which are dispersible in water are also obtained by homogenizing and precomminuting 25 parts by weight of a compound of the formula (I)
5 parts by weight of sodium 2,2'-dinaphthylmethane-6,6'-disulfonate,
2 parts by weight of sodium oleolymethyltaurate,
1 parts by weight of polyvinyl alcohol,
17 parts by weight of calcium carbonate and
50 parts by weight of water, then grinding in a bead mill and atomizing the suspension thus obtained in a spray tower by means of a single substance nozzle and drying.

g) Extruder granules are obtained by mixing 20 parts by weight of active compound, 3 parts by weight of sodium ligninsulfonate, 1 part by weight of carboxymethylcellulose and 76 parts by weight of kaolin, grinding and moistening with water. This mixture is extruded and then dried in a stream of air.

C. BIOLOGICAL EXAMPLES

1. Weed action pre-emergence

Seeds or pieces of rhizome of monocotyledon and dicotyledon weed plants were planted in sandy loam soil in plastic pots and covered with earth. The compounds according to the invention formulated in the form of wettable powders or emulsion concentrates were then applied in various dosages to the surface of the covering earth as aqueous suspensions or emulsions using a water application rate of 600 to 800 l/ha after conversion.

After the treatment, the pots were placed in a greenhouse and kept under good growth conditions for the weeds. Visual assessment of the plants and the emergence damage was carried out in comparison to untreated controls after the emergence of the experiment plants after an experiment time of 3 to 4 weeks. As the assessment values show, the compounds according to the invention have a good herbicidal pre-emergence activity against a broad spectrum of weed grasses and weeds (cf. Table 5).

TABLE 5

Preemergence action of the compounds according to the invention

| Ex. No. | Dose (kg a.i./ha) | Herbicidal action | | | | | |
|---|---|---|---|---|---|---|---|
| | | LOMU | ECCR | AVSA | STME | CHSE | SIAL |
| 1 | 0.3 | 5 | 5 | 5 | 5 | 5 | 5 |
| 136 | 0.3 | 5 | 5 | 4 | 5 | 5 | 5 |
| 4 | 0.3 | 5 | 5 | 5 | 5 | 5 | 5 |
| 411 | 0.3 | 5 | 5 | 5 | 5 | 5 | 5 |
| 354 | 0.3 | 5 | 5 | 5 | 5 | 5 | 5 |
| 439 | 0.3 | 5 | 5 | 5 | 5 | 5 | 5 |
| 312 | 0.3 | 4 | 4 | 2 | 4 | 4 | 5 |
| 326 | 0.3 | 2 | 2 | 2 | 3 | 3 | 4 |
| 7 | 0.3 | 5 | 5 | 5 | 5 | 5 | 5 |
| 299 | 0.3 | 5 | 5 | 4 | 5 | 5 | 5 |
| 443 | 0.3 | 5 | 5 | 5 | 5 | 5 | 5 |

TABLE 5-continued

Preemergence action of the compounds according to the invention

| Ex. No. | Dose (kg a.i./ha) | Herbicidal action | | | | | |
|---|---|---|---|---|---|---|---|
| | | LOMU | ECCR | AVSA | STME | CHSE | SIAL |
| 301 | 0.3 | 2 | 2 | 2 | 2 | 2 | 3 |
| 298 | 0.3 | 5 | 5 | 4 | 5 | 5 | 5 |
| 313 | 0.3 | 3 | 3 | 2 | 4 | 3 | 5 |
| 446 | 0.3 | 5 | 3 | 5 | 4 | 3 | 5 |
| 445 | 0.3 | 5 | 4 | 5 | 5 | 2 | 4 |
| 756 | 0.3 | 5 | 5 | 5 | 5 | 5 | 5 |
| 442 | 0.3 | 5 | 5 | 5 | 5 | 5 | 5 |
| 455 | 0.3 | 3 | 2 | 2 | 3 | 3 | 5 |
| 770 | 0.3 | 5 | 5 | 5 | 5 | 5 | 5 |
| 854 | 0.3 | 5 | 5 | 5 | 5 | 5 | 5 |
| 8 | 0.3 | 5 | 5 | 5 | 5 | 5 | 5 |
| 5 | 0.3 | 5 | 5 | 5 | 5 | 5 | 5 |
| 142 | 0.3 | 5 | 5 | 5 | 5 | 5 | 5 |
| 340 | 0.3 | 5 | 5 | 3 | 5 | 5 | 5 |
| 573 | 0.3 | 5 | 5 | 5 | 5 | 5 | 5 |

Abbreviations:
Ex. No. = Preparation example from Tables 1 to 4
a.i. = active ingredient (based on pure active compound)
LOMU = *Lolium multiflorum*
ECCR = *Echinochloa crus-galli*
AVSA = *Avena sativa*
STME = *Stellaria media*
CHSE = *Chrysanthemum segetum*
STAL = *Sinapis alba*

2. Weed action post-emergence

Seeds or pieces of rhizome of monocotyledon and dicotyledon weeds were planted in sandy loam soil in plastic pots, covered with earth and raised in a greenhouse under good growth conditions. Three weeks after sowing, the experimental plants were treated in the three-leaf stage.

The compounds according to the invention formulated as wettable powders or as emulsion concentrates were sprayed onto the green parts of plants in various dosages using a water application rate of 600 to 800 l/ha after conversion and, after a standing time of the experimental plants in the greenhouse under optimum growth conditions of about 3 to 4 weeks, the action of the preparations was assessed visually in comparison to untreated controls.

The agents according to the invention also show a good herbicidal activity post-emergence against a broad spectrum of economically important weed grasses and weeds (cf. Table 6).

TABLE 6

| Ex. No. | Dose (kg a.i./ha) | Herbicidal action | | | | | |
|---|---|---|---|---|---|---|---|
| | | LOMU | ECCR | AVSA | STME | CHSE | SIAL |
| 1 | 0.3 | 5 | 5 | 5 | 5 | 5 | 5 |
| 136 | 0.3 | 3 | 4 | 1 | 5 | 5 | 5 |
| 4 | 0.3 | 5 | 5 | 5 | 5 | 5 | 5 |
| 411 | 0.3 | 5 | 5 | 4 | 5 | 5 | 5 |
| 354 | 0.3 | 5 | 5 | 5 | 5 | 5 | 5 |
| 439 | 0.3 | 5 | 5 | 5 | 5 | 5 | 5 |
| 7 | 0.3 | 5 | 5 | 5 | 5 | 5 | 5 |
| 299 | 0.3 | 3 | 3 | 2 | 3 | 2 | 5 |
| 443 | 0.3 | 5 | 5 | 5 | 5 | 3 | 5 |
| 298 | 0.3 | 3 | 5 | 2 | 4 | 3 | 5 |
| 445 | 0.3 | 3 | 2 | 2 | 3 | 4 | 3 |
| 756 | 0.3 | 5 | 4 | 3 | 4 | 4 | 5 |
| 442 | 0.3 | 5 | 2 | 3 | 3 | 2 | 4 |
| 770 | 0.3 | 5 | 3 | 3 | 3 | 3 | 3 |
| 854 | 0.3 | 4 | 5 | 4 | 4 | 5 | 5 |

TABLE 6-continued

| Ex. No. | Dose (kg a.i./ha) | Herbicidal action | | | | | |
|---|---|---|---|---|---|---|---|
| | | LOMU | ECCR | AVSA | STME | CHSE | SIAL |
| 8 | 0.3 | 5 | 5 | 5 | 5 | 3 | 5 |
| 5 | 0.3 | 5 | 5 | 5 | 5 | 5 | 5 |
| 142 | 0.3 | 4 | 2 | 2 | 4 | 1 | 3 |
| 340 | 0.3 | 3 | 3 | 0 | 5 | 2 | 5 |
| 573 | 0.3 | 5 | 5 | 5 | 5 | 5 | 5 |

Abbreviations:
Ex. No. = Preparation example from Tables 1 to 4
a.i. = active ingredient (based on pure active compound)
LOMU = *Lolium multiflorum*
ECCR = *Echinochloa crus-galli*
AVSA = *Avena sativa*
STME = *Stellaria media*
CHSE = *Chrysanthemum segetum*
STAL = *Sinapis alba*

3. Crop plant tolerability

In further experiments in a greenhouse, seeds of a relatively large number of crop plants and weeds were planted in sandy loam soil and covered with earth.

Some of the pots were immediately treated as described under 1 and the others were placed in a greenhouse until the plants had developed two to three true leaves and then sprayed with the substances according to the invention in various dosages, as described under 2.

Four to five weeks after application and standing in a greenhouse, it was determined by means of optical assessment that the compounds according to the invention left dicotyl crops such as, for example, soya, cotton, rape, sugarbeet and potatoes undamaged pre- and post-emergence even at high active compound dosages. Moreover, some substances also spared gramineous crops such as, for example, barley, wheat, rye, sorghum millet, corn and rice. The compounds of the formula (I) thus have a high selectivity when used for controlling undesired plant growth in agricultural crops.

We claim:

1. A compound of the formula (II)

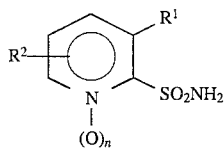

(II)

in which $R^1$ is $-NR^6R^7$, $R^2$ is H, $(C_1-C_4)$alkyl, $(C_1-C_3)$haloalkyl, halogen, $NO_2$, CN, $(C_1-C_3)$alkoxy, $(C_1-C_3)$haloalkoxy, $(C_1-C_3)$alkylthio, $(C_1-C_3)$alkoxy-$(C_1-C_3)$alkyl, $(C_1-C_3)$alkoxycarbonyl, $(C_1-C_3)$alkylamino, di($(C_1-C_3)$alkyl)amino, $(C_1-C_3)$alkylsulfinyl, $(C_1-C_3)$alkylsulfonyl, $SO_2NR^aR^b$ or $C(O)NR^aR^b$, $R^a$ and $R^b$ independently of one another are H, $(C_1-C_3)$alkyl, $(C_3-C_4)$alkenyl, or propargyl;

$R^6$ is H, $(C_1-C_8)$alkyl, which is unsubstituted or substituted by one or more halogen atoms, $(C_1-C_4)$alkoxy, $(C_1-C_4)$alkylthio, $(C_1-C_4)$alkylsulfinyl, $(C_1-C_4)$alkylsulfonyl, $(C_1-C_4)$alkoxycarbonyl or CN, or is $(C_3-C_6)$alkenyl which is unsubstituted or substituted by one or more halogen atoms, or is $(C_3-C_6)$alkynyl which is unsubstituted or substituted by one or more halogen atoms, or is $(C_1-C_4)$alkylsulfonyl which is unsubstituted or substituted by one or more halogen atoms, or is phenylsulfonyl where the phenyl radical is unsubstituted or substituted by one or more halogen atoms, $(C_1-C_4)$alkyl or $(C_1-C_4)$alkoxy, or is $(C_1-C_4)$alkoxy or $(C_1-C_4)$alkylcarbonyl which is unsubstituted or substituted by one or more halogen atoms, $R^7$ is $(C_1-C_4)$alkylsulfonyl which is unsubstituted or substituted by one or more halogen atoms, phenylsulfonyl where the phenyl radical is unsubstituted or substituted by one or more halogen atoms, $(C_1-C_4)$alkyl or $(C_1-C_4)$alkoxy, or is (di-$(C_1-C_4)$alkyl)aminosulfonyl or $R^6$ and $R^7$ together are a chain of the formula $-(CH_2)_m-SO_2$, where m is 3 or 4, and n is zero or 1.

2. A compound according to claim 1:

in which $R^1$ is $-NR^6R^7$, $R^2$ is H, $(C_1-C_3)$alkyl, $(C_1-C_3)$haloalkyl, halogen, $NO_2$, CN, $(C_1-C_3)$alkoxy, $(C_1-C_3)$haloalkoxy, $(C_1-C_3)$alkylthio, $(C_1-C_3)$alkoxy-$(C_1-C_3)$alkyl, $(C_1-C_3)$alkoxy-carbonyl, $(C_1-C_3)$alkylamino, di($(C_1-C_3)$alkyl)amino, $(C_1-C_3)$alkylsulfinyl, $(C_1-C_3)$alkylsulfonyl, $SO_2NR^aR^b$ or $C(O)NR^aR^b$, $R^a$ and $R^b$ independently of one another are H, $(C_1-C_3)$alkyl, $(C_3-C_4)$alkenyl, propargyl;

$R^6$ is H, $(C_1-C_4)$alkyl, $(C_1-C_4)$alkylsulfonyl, phenylsulfonyl where the phenyl radical is optionally substituted by one or more halogen atoms, $(C_1-C_4)$alkyl or $(C_1-C_4)$alkoxy, or is $(C_3-C_4)$alkenyl or $(C_3-C_4)$alkynyl, $R^7$ is $(C_1-C_4)$alkylsulfonyl or phenylsulfonyl where the phenyl radical is optionally substituted by one or more halogen atoms, $(C_1-C_4)$alkyl or $(C_1-C_4)$alkoxy, and n is zero or 1.

3. A compound as claimed in claim 2 wherein $R^2$ is $(C_1-C_3)$alkyl, $(C_1-C_3)$alkoxy, halogen or $(C_1-C_3)$alkylthio, $R^6$ is hydrogen, $(C_1-C_3)$alkyl or $(C_1-C_3)$alkylsulfonyl, and $R^7$ is $(C_1-C_3)$alkylsulfonyl.

4. A compound according to claim 1 wherein $R^1$ is $NR^6R^7$ $R^2$ is H, a $(C_1-C_3)$alkyl group, a $(C_1-C_3)$haloalkyl group, halogen, a $(C_1-C_3)$alkoxy group, a $(C_1-C_3)$alkylthio group, a $(C_1-C_3)$alkoxy-$(C_1-C_3)$alkyl group, a $(C_1-C_3)$alkylamino group or a diamino group, $R^6$ is H, a $(C_1-C_4)$alkyl group, or a $(C_3-C_4)$alkenyl group, $R^7$ is $(C_1-C_4)$alkylsulfonyl, and n is zero.

5. The compound according to claim 4 wherein $R^7$ is a $(C_1-C_4)$alkylsulfonyl, $R^6$ is a $(C_1-C_4)$alkyl group, and $R^2$ is substituted in the 6-position in the ring and is a hydrogen atom, a halogen atom, a $(C_1-C_3)$alkyl group, a $(C_1-C_3)$haloalkyl group, a $(C_1-C_3)$alkoxy group or a $(C_1-C_3)$alkoxy-$(C_1-C_3)$alkyl group.

6. The compound according to claim 5, wherein $R^7$ is a $(C_1-C_4)$alkylsulfonyl group, and $R^2$ is a hydrogen atom, a halogen atom, a ($C_1$-$C_3$)alkyl group or a ($C_1$-$C_3$)alkoxy group.

7. The compound according to claim 5, wherein $R^7$ is methylsulfonyl, $R^6$ is a methyl group, and $R^2$ is a hydrogen atom, a halogen atom, a ($C_1$-$C_3$)alkyl group or a ($C_1$-$C_3$)alkoxy group.

8. A compound according to claim 1 wherein:
$R^1$ is —$NR^6R^7$ in which $R^6$ is H and $R^7$ is methylsulfonyl such that $R^1$ is —$NHSO_2CH_3$; $R^2$ is H, 4—$CH_3$, 6—$CH_3$, 4—Cl, 6—Cl, 6—F or 6—$OCH_3$; and, n is zero.

9. A compound according to claim 1 wherein:
$R^1$ is —$NR^6R^7$ in which $R^6$ is H and $R^7$ is ethylsulfonyl such that $R^1$ is —$NHSO_2C_2H_5$; $R^2$ is H, 4—$CH_3$, 6—$CH_3$, 4—Cl, 6—Cl, 6—F or 6—$OCH_3$; and n is zero.

10. A compound according to claim 1 wherein:
$R^1$ is —$NR^6R^7$ in which $R^6$ is H and $R^7$ is propylsulfonyl such that $R^1$ is —$NHSO_2C_3H_7$; $R^2$ is H, 4—$CH_3$, 6—$CH_3$, 4—Cl, 6—Cl, 6—F or 6—$OCH_3$; and n is zero.

11. A compound according to claim 1 wherein:
$R^1$ is —$NR^6R^7$ in which $R^6$ is —$CH_3$ and $R^7$ is methylsulfonyl such that $R^1$ is —$N(CH_3)SO_2CH_3$; $R^2$ is H, 4—$CH_3$, 6—$CH_3$, 4—Cl, 6—Cl, 6—F or 6—$OCH_3$; and n is zero.

12. A compound according to claim 1 wherein:
$R^1$ is —$NR^6R^7$ in which $R^6$ is —$CH_3$ and $R^7$ is ethylsulfonyl such that $R^1$ is —$N(CH_3)SO_2C_2H_5$; $R^2$ is H, 4—$CH_3$, 6—$CH_3$, 4—Cl, 6—Cl, 6—F or 6—$OCH_3$; and n is zero.

13. A compound according to claim 1 wherein:
$R^1$ is —$NR^6R^7$ in which $R^6$ is —$C_2H_5$ and $R^7$ is methylsulfonyl such that $R^1$ is —$N(C_2H_5)SO_2CH_3$; $R^2$ is H, 4—$CH_3$, 6—$CH_3$, 4—Cl, 6—Cl, 6—F or 6—$OCH_3$; and n is zero.

14. A compound according to claim 1 wherein:
$R^1$ is —$NR^6R^7$ in which $R^6$ is —$C_3H_7$ and $R^7$ is methylsulfonyl such that $R^1$ is —$N(C_3H_7)SO_2CH_3$; $R^2$ is H, 4—$CH_3$, 6—$CH_3$, 4—Cl, 6—Cl, 6—F or 6—$OCH_3$; and n is zero.

15. A compound as claimed in claim 8 wherein $R^2$ is H.
16. A compound as claimed in claim 8 wherein $R^2$ is 4—$CH_3$.
17. A compound as claimed in claim 8 wherein $R^2$ is 4—Cl.
18. A compound as claimed in claim 8 wherein $R^2$ is 6—$CH_3$.
19. A compound as claimed in claim 8 wherein $R^2$ is 6—$OCH_3$.
20. A compound as claimed in claim 8 wherein $R^2$ is 6—Cl.
21. A compound as claimed in claim 8 wherein $R^2$ is 6—F.
22. A compound as claimed in claim 9 wherein $R^2$ is H.
23. A compound as claimed in claim 9 wherein $R^2$ is 4—$CH_3$.
24. A compound as claimed in claim 9 wherein $R^2$ is 4—Cl.
25. A compound as claimed in claim 9 wherein $R^2$ is 6—$CH_3$.
26. A compound as claimed in claim 9 wherein $R^2$ is 6—$OCH_3$.
27. A compound as claimed in claim 9 wherein $R^2$ is 6—Cl.
28. A compound as claimed in claim 9 wherein $R^2$ is 6—F.
29. A compound as claimed in claim 10 wherein $R^2$ is H.
30. A compound as claimed in claim 10 wherein $R^2$ is 4—$CH_3$.
31. A compound as claimed in claim 10 wherein $R^2$ is 4—Cl.
32. A compound as claimed in claim 10 wherein $R^2$ is 6—$CH_3$.
33. A compound as claimed in claim 10 wherein $R^2$ is 6—$OCH_3$.
34. A compound as claimed in claim 10 wherein $R^2$ is 6—Cl.
35. A compound as claimed in claim 10 wherein $R^2$ is 6—F.
36. A compound as claimed in claim 11 wherein $R^2$ is H.
37. A compound as claimed in claim 11 wherein $R^2$ is 4—$CH_3$.
38. A compound as claimed in claim 11 wherein $R^2$ is 4—Cl.
39. A compound as claimed in claim 11 wherein $R^2$ is 6—$CH_3$.
40. A compound as claimed in claim 11 wherein $R^2$ is 6—$OCH_3$.
41. A compound as claimed in claim 11 wherein $R^2$ is 6Cl.
42. A compound as claimed in claim 11 wherein $R^2$ is 6—F.
43. A compound as claimed in claim 12 wherein $R^2$ is H.
44. A compound as claimed in claim 12 wherein $R^2$ is 4—$CH_3$.
45. A compound as claimed in claim 12 wherein $R^2$ is 4—Cl.
46. A compound as claimed In claim 12 wherein $R^2$ is 6—$CH_3$.
47. A compound as claimed in claim 12 wherein $R^2$ is 6—$OCH_3$.
48. A compound as claimed in claim 12 wherein $R^2$ is 6—Cl.
49. A compound as claimed in claim 12 wherein $R^2$ is 6—F.
50. A compound as claimed in claim 13 wherein $R^2$ is H.
51. A compound as claimed in claim 13 wherein $R^2$ is 4—$CH_3$.
52. A compound as claimed in claim 13 wherein $R^2$ is 4—Cl.
53. A compound as claimed in claim 13 wherein $R^2$ is 6—$CH_3$.
54. A compound as claimed in claim 13 wherein $R^2$ is 6—$OCH_3$.
55. A compound as claimed in claim 13 wherein $R^2$ is 6—Cl.
56. A compound as claimed in claim 13 wherein $R^2$ is 6—F.
57. A compound as claimed in claim 14 wherein $R^2$ is H.
58. A compound as claimed in claim 14 wherein $R^2$ is 4—$CH_3$.
59. A compound as claimed in claim 14 wherein $R^2$ is 4—Cl.
60. A compound as claimed in claim 14 wherein $R^2$ is 6—$CH_3$.
61. A compound as claimed in claim 14 wherein $R^2$ is 6—$OCH_3$.
62. A compound as claimed in claim 14 wherein $R^2$ is 6—Cl.
63. A compound as claimed in claim 14 wherein $R^2$ is 6—F.
64. A compound according to claim 1 in which:
n is zero,
$R^1$ is —$NR^6R^7$,
$R^2$ is H, $R^6$ is methyl, $R^7$ is methylsulfonyl; or $R^2$ is H, $R^6$ is ethyl, $R^7$ is methylsulfonyl; or
$R^2$ is H, $R^6$ is methyl, $R^7$ is ethylsulfonyl; or
$R^2$ is H, $R^6$ is H, $R^7$ is methylsulfonyl; or
$R^2$ is 6—$CH_3$, $R^6$ is methyl, $R^7$ is methylsulfonyl; or
$R^2$ is 6—$OCH_3$, $R^6$ is methyl, $R^7$ is methylsulfonyl; or
$R^2$ is 6—Cl, $R^6$ is methyl, $R^7$ is methylsulfonyl; or
$R^2$ is 6—F, $R^6$ is methyl, $R^7$ is methylsulfonyl.

65. A compound according to claim 1 wherein:

n is zero;

$R^1$ is —$NHSO_2CH_3$, —$NHSO_2C_2H_5$, —$NHSO_2C_3H_7$, —$N(CH_3)SO_2CH_3$, —$N(C_2H_5)SO_2CH_3$, —$N(C_3H_7)SO_2CH_3$, or —$N(CH_3)SO_2C_2H_5$; and $R^2$ is H, methyl, chlorine, fluorine, or methoxy.

* * * * *